(12) United States Patent
Allavatam et al.

(10) Patent No.: US 12,076,574 B2
(45) Date of Patent: Sep. 3, 2024

(54) CARDIAC BEAT CLASSIFICATION TO AVOID DELIVERING SHOCK DURING VENTRICULAR REPOLARIZATION

(71) Applicant: CARDIAC PACEMAKERS, INC., St. Paul, MN (US)

(72) Inventors: Venugopal Allavatam, Saratoga, CA (US); Benjamin Speakman, Eagan, MN (US); Leanne M. Eberle, Mahtomedi, MN (US)

(73) Assignee: CARDIAC PACEMAKERS, INC.

( * ) Notice: Subject to any disclaimer, the term of this patent is extended or adjusted under 35 U.S.C. 154(b) by 292 days.

(21) Appl. No.: 17/496,511

(22) Filed: Oct. 7, 2021

(65) Prior Publication Data
US 2022/0111220 A1 Apr. 14, 2022

Related U.S. Application Data

(60) Provisional application No. 63/089,152, filed on Oct. 8, 2020.

(51) Int. Cl.
*A61N 1/39* (2006.01)
(52) U.S. Cl.
CPC ......... *A61N 1/3987* (2013.01); *A61N 1/3956* (2013.01); *A61N 1/3981* (2013.01)
(58) Field of Classification Search
CPC ... A61N 1/3956; A61N 1/3904; A61N 1/3987
See application file for complete search history.

(56) References Cited

U.S. PATENT DOCUMENTS

| | | | |
|---|---|---|---|
| 3,738,370 | A | 6/1973 | Charms |
| 4,184,493 | A | 1/1980 | Langer et al. |
| 4,300,567 | A | 11/1981 | Kolenik et al. |
| 4,384,585 | A | 5/1983 | Zipes |
| 4,407,288 | A | 10/1983 | Langer et al. |
| 4,450,527 | A | 5/1984 | Sramek |

(Continued)

FOREIGN PATENT DOCUMENTS

| | | |
|---|---|---|
| EP | 0554208 A2 | 8/1993 |
| EP | 1820535 A1 | 8/2007 |

(Continued)

OTHER PUBLICATIONS

International Search Report and Written Opinion dated Jan. 24, 2022 for International Application No. PCT/US2021/053998.

(Continued)

*Primary Examiner* — George R Evanisko
(74) *Attorney, Agent, or Firm* — Seager, Tufte & Wickhem LLP

(57) ABSTRACT

Wearable, automatic external, and implantable defibrillators, as well as methods of operation in such systems, are disclosed with shock delivery mitigations to avoid delivering a defibrillation shock on a T-wave. Prior to issuance of a defibrillation shock, one or more detected cardiac events are analyzed to characterize a detected event that is sensed for purposes of synchronizing the defibrillation shock. The detected event can be characterized as an R-wave or a T-wave, and the shock delivery protocol is then selected based on the characterization of the detected event to avoid shock-on-T and potential pro-arrhythmia.

10 Claims, 14 Drawing Sheets

(56) References Cited

U.S. PATENT DOCUMENTS

| | | | |
|---|---|---|---|
| 4,457,315 | A | 7/1984 | Bennish |
| 4,595,009 | A | 6/1986 | Leinders |
| 4,679,144 | A | 7/1987 | Cox et al. |
| 4,693,253 | A | 9/1987 | Adams |
| 4,750,494 | A | 6/1988 | King |
| 4,779,617 | A | 10/1988 | Whigham |
| 4,979,110 | A | 12/1990 | Albrecht et al. |
| 4,989,602 | A | 2/1991 | Sholder et al. |
| 5,000,189 | A | 3/1991 | Throne et al. |
| 5,105,810 | A | 4/1992 | Collins et al. |
| 5,179,945 | A | 1/1993 | Van Hofwegen et al. |
| 5,184,616 | A | 2/1993 | Weiss |
| 5,188,105 | A | 2/1993 | Keimel |
| 5,190,034 | A | 3/1993 | Sholder |
| 5,191,884 | A | 3/1993 | Gilli et al. |
| 5,193,535 | A | 3/1993 | Bardy et al. |
| 5,215,098 | A | 6/1993 | Steinhaus et al. |
| 5,217,021 | A | 6/1993 | Steinhaus et al. |
| 5,251,625 | A | 10/1993 | Wilson et al. |
| 5,257,621 | A | 11/1993 | Bardy et al. |
| 5,271,411 | A | 12/1993 | Ripley et al. |
| 5,280,792 | A | 1/1994 | Leong et al. |
| 5,299,119 | A | 3/1994 | Kraf et al. |
| 5,313,953 | A | 5/1994 | Yomtov et al. |
| 5,330,504 | A | 7/1994 | Somerville et al. |
| 5,331,966 | A | 7/1994 | Bennett et al. |
| 5,342,402 | A | 8/1994 | Olson et al. |
| 5,342,407 | A | 8/1994 | Dahl et al. |
| 5,350,402 | A * | 9/1994 | Infinger ............... A61N 1/3622 607/5 |
| 5,351,696 | A | 10/1994 | Riff et al. |
| 5,376,104 | A | 12/1994 | Sakai et al. |
| 5,423,326 | A | 6/1995 | Wang et al. |
| 5,447,519 | A | 9/1995 | Peterson |
| 5,464,430 | A | 11/1995 | Rossing |
| 5,464,431 | A | 11/1995 | Adams et al. |
| 5,486,198 | A * | 1/1996 | Ayers ............... A61N 1/3918 600/518 |
| 5,489,293 | A | 2/1996 | Pless et al. |
| 5,522,852 | A | 6/1996 | White et al. |
| 5,534,019 | A | 7/1996 | Paspa |
| 5,545,186 | A | 8/1996 | Olson et al. |
| 5,558,098 | A | 9/1996 | Fain |
| 5,578,062 | A | 11/1996 | Alt et al. |
| 5,601,609 | A | 2/1997 | Duncan |
| 5,607,455 | A | 3/1997 | Armstrong |
| 5,658,317 | A | 8/1997 | Haefner et al. |
| 5,709,215 | A | 1/1998 | Perttu et al. |
| 5,755,736 | A | 5/1998 | Gillberg et al. |
| 5,766,225 | A | 6/1998 | Kramm |
| 5,792,192 | A | 8/1998 | Lu |
| 5,817,134 | A | 10/1998 | Greenhut et al. |
| 5,827,197 | A | 10/1998 | Bocek et al. |
| 5,857,977 | A | 1/1999 | Caswell et al. |
| 5,944,669 | A | 8/1999 | Kaib |
| 5,991,657 | A | 11/1999 | Kim |
| 6,041,251 | A | 3/2000 | Kim et al. |
| 6,047,210 | A | 4/2000 | Kim et al. |
| 6,052,617 | A | 4/2000 | Kim |
| 6,058,328 | A | 5/2000 | Levine et al. |
| 6,065,154 | A | 5/2000 | Hulings et al. |
| 6,095,987 | A | 8/2000 | Shmulewitz et al. |
| 6,115,628 | A | 9/2000 | Stadler et al. |
| 6,144,879 | A | 11/2000 | Gray |
| 6,148,230 | A | 11/2000 | Kenknight |
| 6,169,923 | B1 | 1/2001 | Kroll |
| 6,223,078 | B1 | 4/2001 | Marcovecchio |
| 6,230,055 | B1 | 5/2001 | Sun et al. |
| 6,236,882 | B1 | 5/2001 | Lee et al. |
| 6,240,313 | B1 | 5/2001 | Esler |
| 6,266,554 | B1 | 7/2001 | Hsu et al. |
| 6,280,462 | B1 | 8/2001 | Hauser et al. |
| 6,308,095 | B1 | 10/2001 | Hsu et al. |
| 6,334,071 | B1 | 12/2001 | Lu |
| 6,377,844 | B1 | 4/2002 | Graen |
| 6,381,493 | B1 | 4/2002 | Stadler et al. |
| 6,393,316 | B1 | 5/2002 | Gillberg et al. |
| 6,397,100 | B2 | 5/2002 | Stadler et al. |
| 6,411,844 | B1 | 6/2002 | Kroll et al. |
| 6,438,410 | B2 | 8/2002 | Hsu et al. |
| 6,449,503 | B1 | 9/2002 | Hsu |
| 6,493,579 | B1 | 12/2002 | Gilkerson et al. |
| 6,493,584 | B1 | 12/2002 | Lu |
| 6,505,068 | B2 | 1/2003 | Bonnet et al. |
| 6,516,225 | B1 | 2/2003 | Florio |
| 6,561,984 | B1 | 5/2003 | Turcott |
| 6,567,691 | B1 | 5/2003 | Stadler |
| 6,574,505 | B1 | 6/2003 | Warren |
| 6,575,912 | B1 | 6/2003 | Turcott |
| 6,587,720 | B2 | 7/2003 | Hsu et al. |
| 6,625,490 | B1 | 9/2003 | Mcclure et al. |
| 6,643,549 | B1 | 11/2003 | Bradley et al. |
| 6,647,292 | B1 | 11/2003 | Bardy et al. |
| 6,684,100 | B1 | 1/2004 | Sweeney et al. |
| 6,699,200 | B2 | 3/2004 | Cao et al. |
| 6,708,058 | B2 | 3/2004 | Kim et al. |
| 6,708,062 | B2 | 3/2004 | Ericksen et al. |
| 6,721,597 | B1 | 4/2004 | Bardy et al. |
| 6,728,572 | B2 | 4/2004 | Hsu et al. |
| 6,731,978 | B2 | 5/2004 | Olson et al. |
| 6,745,068 | B2 | 6/2004 | Koyrakh et al. |
| 6,754,528 | B2 | 6/2004 | Bardy et al. |
| 6,889,079 | B2 | 5/2005 | Bocek et al. |
| 6,909,916 | B2 | 6/2005 | Spinelli et al. |
| 6,950,702 | B2 | 9/2005 | Sweeney |
| 7,016,730 | B2 | 3/2006 | Ternes |
| 7,020,523 | B1 | 3/2006 | Lu et al. |
| 7,027,856 | B2 | 4/2006 | Zhou et al. |
| 7,027,858 | B2 | 4/2006 | Cao et al. |
| 7,027,862 | B2 | 4/2006 | Dahl et al. |
| 7,031,764 | B2 | 4/2006 | Schwartz et al. |
| 7,062,314 | B2 | 6/2006 | Zhu et al. |
| 7,062,315 | B2 | 6/2006 | Koyrakh et al. |
| 7,062,322 | B2 | 6/2006 | Stadler et al. |
| 7,076,289 | B2 | 7/2006 | Sarkar et al. |
| 7,085,599 | B2 | 8/2006 | Kim et al. |
| 7,117,035 | B2 | 10/2006 | Wagner et al. |
| 7,149,575 | B2 | 12/2006 | Ostroff et al. |
| 7,162,301 | B2 | 1/2007 | Kim et al. |
| 7,167,747 | B2 | 1/2007 | Gunderson et al. |
| 7,181,273 | B2 | 2/2007 | Havel et al. |
| 7,184,815 | B2 | 2/2007 | Kim et al. |
| 7,184,818 | B2 | 2/2007 | Kim et al. |
| 7,191,004 | B2 | 3/2007 | Kim et al. |
| 7,194,302 | B2 | 3/2007 | Bardy et al. |
| 7,218,966 | B2 | 5/2007 | Haefner |
| 7,236,819 | B2 | 6/2007 | Brockway et al. |
| 7,248,921 | B2 | 7/2007 | Palreddy et al. |
| 7,266,409 | B2 | 9/2007 | Gunderson |
| 7,283,863 | B2 | 10/2007 | Gunderson et al. |
| 7,302,294 | B2 | 11/2007 | Kamath et al. |
| 7,308,305 | B1 | 12/2007 | Province et al. |
| 7,330,757 | B2 | 2/2008 | Ostroff et al. |
| 7,346,392 | B2 | 3/2008 | Kenknight |
| 7,376,458 | B2 | 5/2008 | Palreddy et al. |
| 7,379,772 | B2 | 5/2008 | Bardy et al. |
| 7,386,342 | B1 | 6/2008 | Falkenberg et al. |
| 7,392,085 | B2 | 6/2008 | Warren et al. |
| 7,444,182 | B2 | 10/2008 | Ostroff et al. |
| 7,447,540 | B1 | 11/2008 | Nabutovsky et al. |
| 7,463,922 | B1 | 12/2008 | Snyder et al. |
| 7,467,009 | B2 | 12/2008 | Palreddy et al. |
| 7,477,935 | B2 | 1/2009 | Palreddy et al. |
| 7,496,408 | B2 | 2/2009 | Ghanem et al. |
| 7,496,409 | B2 | 2/2009 | Greenhut et al. |
| 7,499,750 | B2 | 3/2009 | Haefner et al. |
| 7,522,959 | B2 | 4/2009 | Hauser et al. |
| 7,546,159 | B1 | 6/2009 | Nabutovsky et al. |
| 7,555,335 | B2 | 6/2009 | Kamath et al. |
| 7,559,900 | B2 | 7/2009 | Gillberg |
| 7,567,835 | B2 | 7/2009 | Gunderson et al. |
| 7,570,997 | B2 | 8/2009 | Lovett et al. |
| 7,593,771 | B2 | 9/2009 | Yonce et al. |
| 7,623,913 | B2 | 11/2009 | Phillips |

(56) References Cited

U.S. PATENT DOCUMENTS

| | | |
|---|---|---|
| 7,623,916 B2 | 11/2009 | Julian |
| 7,655,014 B2 | 2/2010 | Ko et al. |
| 7,660,629 B2 | 2/2010 | Province et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,769,445 B2 | 8/2010 | Rissmann et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 8,565,878 B2 | 10/2013 | Allavatam et al. |
| 8,594,786 B2 | 11/2013 | Ousdigian |
| 9,149,637 B2 | 10/2015 | Warren et al. |
| 9,636,514 B2 | 5/2017 | Warren et al. |
| 2003/0114888 A1 | 6/2003 | Stadler et al. |
| 2003/0195569 A1 | 10/2003 | Swerdlow et al. |
| 2004/0049120 A1 | 3/2004 | Cao et al. |
| 2004/0215239 A1 | 10/2004 | Favet et al. |
| 2004/0215240 A1 | 10/2004 | Lovett et al. |
| 2004/0220624 A1 | 11/2004 | Ritscher et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian |
| 2006/0122676 A1 | 6/2006 | Ko et al. |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0009906 A1 | 1/2008 | Perschbacher et al. |
| 2008/0015647 A1 | 1/2008 | Palreddy et al. |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2009/0018595 A1 | 1/2009 | Bharmi et al. |
| 2009/0036788 A1 | 2/2009 | Nabutovsky et al. |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0131998 A1 | 5/2009 | Warren et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0228057 A1 | 9/2009 | Allavatam et al. |
| 2009/0240157 A1 | 9/2009 | Lian et al. |
| 2009/0240300 A1 | 9/2009 | Ian et al. |
| 2009/0259271 A1 | 10/2009 | Allavatam et al. |
| 2010/0004713 A1 | 1/2010 | Warren et al. |
| 2010/0106209 A1 | 4/2010 | Gunderson et al. |
| 2010/0331904 A1 | 12/2010 | Warren et al. |
| 2016/0136447 A1* | 5/2016 | Herleikson ............ A61N 1/395 607/7 |

FOREIGN PATENT DOCUMENTS

| | | |
|---|---|---|
| JP | 2005512629 A | 5/2005 |
| JP | 2006524106 A | 10/2006 |
| JP | 2006525092 A | 11/2006 |
| JP | 2008528103 A | 7/2008 |
| JP | 2012532633 A | 12/2012 |
| WO | 2004091719 A2 | 10/2004 |
| WO | 20060810027 A2 | 8/2006 |
| WO | 2011008550 A1 | 1/2011 |
| WO | 2014199257 A1 | 12/2014 |
| WO | 2014199291 A1 | 12/2014 |

OTHER PUBLICATIONS

Gunderson et al; "An Algorithm to Predict Implantable Cardioverter-Defibrillator Lead Failure," JACC, vol. 44, No. 9, pp. 1898-1902.

Olson et al.; "Onset and Stability for Ventricular Tachyarrhythmia Detection in an Implantable Pacer-Defibrillator," IEEE, pp. 167-170, 1987.

Schuder, "The Role of an Engineering Oriented Medical Research Group in Developing Improved Methods and Devices for Achieving Ventricular Defibrillation: The University of Missouri Experience," PACE, vol. 16,pp. 95-124. Jan. 1993.

Schwake et al; "Komplikationen nit Sonden bei 340 Patienten mit einem Implantierbaren Kardioverter/Defibrillator," Z Kardiol vol. 88, No. 8, pp. 559-565, 1999.

Swerdlow et al; "Advanced ICD Troubleshooting: Part I," online article at http://www.medscape.com/viewarticle/520588_print, accessed and printed Jul. 7, 2009, indicates publication Jan. 9, 2006 (publication date not confirmed).

Throne, "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, pp. 561-570, Jun. 1991.

U.S. Appl. No. 61/255,253, filed Oct. 27, 2009; Allavatam et al.

Australian Application Serial No. 2010273710, Voluntary Amendment 5 pages, filed Jan. 16, 2012.

International Application Serial No. PCT/US2010/040419, International Preliminary Report on Patentability, 11 pgs. mailed Jan. 12, 2012.

International Application Serial No. PCT/US2010/040419, International Search Report mailed Nov. 10, 2010 4 pgs.

International Application Serial No. PCT/US2010/040419, Written Opinion mailed Nov. 10, 2010, 9 pgs.

"Chinese Application Serial No. 201080038609.8, Office Action mailed Dec. 6, 2013", With English Translation , 21 pgs.

"Japanese Application Serial No. 2012-517859, Office Action mailed May 7, 2014", (W/English Translation), 5 pgs.

"Japanese Application Serial No. 2012-517859, Response filed Aug. 7, 2014, to Office Action mailed May 7, 2014", (W/English Translation), 5 pgs.

* cited by examiner

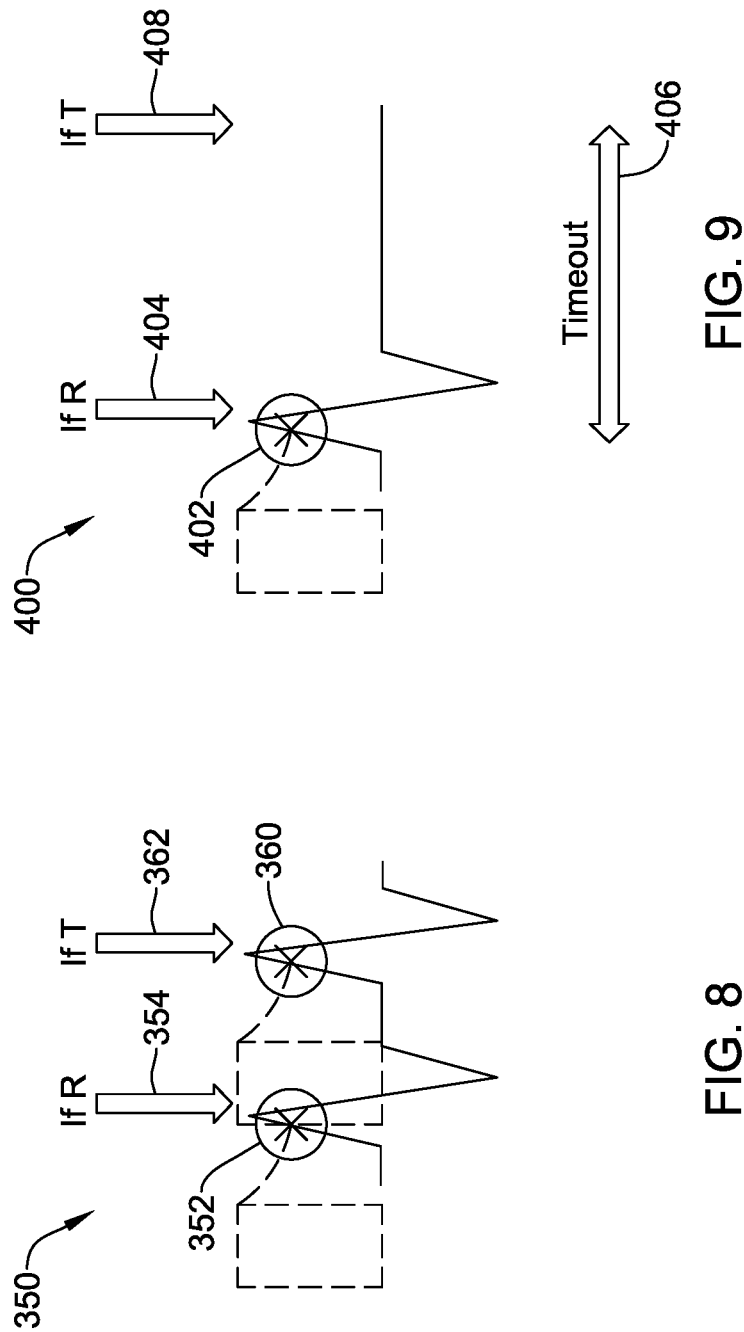

CARDIAC BEAT CLASSIFICATION TO AVOID DELIVERING SHOCK DURING VENTRICULAR REPOLARIZATION

CROSS REFERENCE TO RELATED APPLICATIONS

The present application claims the benefit of and priority to U.S. Provisional Patent Application No. 63/089,152, filed Oct. 8, 2020 and titled CARDIAC BEAT CLASSIFICATION TO AVOID DELIVERING SHOCK DURING VENTRICULAR REPOLARIZATION, the disclosure of which is incorporated herein by reference.

BACKGROUND

External, wearable and implantable defibrillators are used to correct an overly fast cardiac rhythm, such as a polymorphic ventricular tachyarrhythmia or a ventricular fibrillation. In operation, the defibrillator senses cardiac rhythms and determines whether or not defibrillation shock therapy is necessary. Typically, if the defibrillator determines a defibrillation shock is needed, high power capacitors are charged to an appropriate energy or voltage level to achieve defibrillation. Once the capacitors are ready for issuing a therapy, the device senses the cardiac rhythm to detect a new cardiac cycle. If a cardiac cycle is detected, the defibrillator issues a "synchronized" therapy after expiration of a short post-detection time interval. If no "beat" is detected, defibrillation therapy is issued asynchronously following expiration of a timeout interval.

Despite decades of efforts to ensure quick, reliable, and accurate decision making, inappropriate shocks are still one of the more prevalent adverse events associated with cardiac defibrillators. Inappropriate shock is painful to the patient, reduces available battery capacity of the device, and can lead to harmful psychological outcomes. In addition, an inappropriate therapy may, in some limited circumstances, be pro-arrhythmic, leading to onset of ventricular fibrillation. For example, a pro-arrhythmic inappropriate shock may occur if the defibrillation shock is issued at a vulnerable time in the cardiac cycle, such as during the T-wave.

Mitigations are needed to reduce the potential for pro-arrhythmic defibrillation shock.

Overview

The present inventors have recognized, among other things, that one cause of potential inappropriate shock is malsensing, such as may occur if the defibrillator senses both cardiac R-waves (ventricular depolarizations) as well as T-waves (ventricular repolarization), which can cause the defibrillator to calculate a cardiac rate that is twice the actual rate. Such overcounting can lead the defibrillator to mistakenly identify a need for therapy delivery, and subsequently to prepare for and issue a defibrillation shock. If T-wave overcounting occurs, there is a risk that the shock therapy will be synchronized to the T-wave, thereby increasing the risk of pro-arrhythmia. The present inventors have identified a need for mitigation strategies applicable to the synchronization of defibrillation shocks that reduce the potential for pro-arrhythmic inappropriate shock, and have developed such mitigations as further described below.

A first illustrative and non-limiting example takes the form of a method of delivering a defibrillation shock in a defibrillator having electrodes for sensing cardiac signals, analysis circuitry for analyzing the sensed cardiac signals, therapy delivery capacitors for storing energy for a defibrillation shock, a charger configured to charge the therapy delivery capacitors, and therapy output circuitry for issuing a defibrillation shock using energy stored on the therapy delivery capacitors; the method comprising: determining a need for a defibrillation shock and charging therapy delivery capacitors for defibrillation shock delivery to a predetermined shock threshold; after completing charging of the therapy delivery capacitors to the predetermined shock threshold: sensing an Nth cardiac electrical event; characterizing the Nth cardiac electrical event as either an R-wave or a T-wave; and: if the Nth cardiac electrical event is an R-wave, issuing the defibrillation shock according to a first shock protocol; or if the Nth cardiac electrical event is a T-wave, issuing the defibrillation shock according to a second shock protocol.

Additionally or alternatively, the step of characterizing the $N^{th}$ cardiac electrical event as either an R-wave or a T-wave includes detecting at least one preceding cardiac electrical event and determining whether one or more of an interval or an amplitude associated with the preceding cardiac electrical event indicates the $N^{th}$ cardiac electrical event is to be characterized as an R-wave or as a T-wave.

Additionally or alternatively, the step of characterizing the $N^{th}$ cardiac electrical event as either an R-wave or a T-wave includes detecting at least one preceding cardiac electrical event and analyzing morphology of the at least one preceding cardiac electrical event to characterize the $N^{th}$ cardiac electrical event as an R-wave or as a T-wave.

Additionally or alternatively, issuing the defibrillation shock according to the first shock protocol comprises issuing the defibrillation shock after expiration of a first shock delay following the Nth cardiac electrical event; and issuing the defibrillation shock according to the second shock protocol comprises issuing the defibrillation shock after expiration of a second shock delay following the Nth cardiac electrical event.

Additionally or alternatively, the method further comprises calculating the second shock delay as follows: sensing each of N-1, N-2, and N-3 cardiac electrical events, where the N-1 cardiac electrical event precedes the Nth cardiac electrical event, the N-2 cardiac electrical event precedes the N-1 cardiac electrical event, and the N-3 cardiac electrical event precedes the N-2 cardiac electrical event, each of the Nth, N-1, N-2, and N-3 cardiac electrical events representing consecutive detections of cardiac events; determining interval I1, representing an interval from the N-1 cardiac electrical event to the Nth cardiac electrical event; determining interval I2, representing an interval from the N-2 cardiac electrical event to the N-1 cardiac electrical event; determining interval I3, representing an interval from the N-3 cardiac electrical event to the N-2 cardiac electrical event; and setting the second shock delay equal to {I2+I3−I1}. Additionally or alternatively, the method may include calculating the first shock delay equal to an average of I2 and I3, minus I1.

Additionally or alternatively, issuing the defibrillation shock according to the second shock protocol comprises sensing a Next cardiac electrical event and: issuing the defibrillation shock after detection of the Next cardiac electrical event, or issuing the defibrillation shock after expiration of a predetermined timeout interval without sensing another cardiac electrical event.

Additionally or alternatively, issuing the defibrillation shock according to the second shock protocol comprises sensing a Next cardiac electrical event and characterizing the Next cardiac electrical event as an R-wave or a T-wave, and: if the Next cardiac electrical event is an R-wave, issuing the defibrillation shock using the first shock protocol after the Next cardiac electrical event; or if the Next cardiac electrical event is a T-wave, either: sensing a Subsequent cardiac electrical event after the Next cardiac electrical event and issuing the defibrillation shock after detection of the Subsequent cardiac electrical event, or issuing the defibrillation shock after expiration of a predetermined timeout interval without sensing another cardiac electrical event after the Next cardiac electrical event.

Additionally or alternatively, the step of characterizing the Nth cardiac electrical event as either an R-wave or a T-wave comprises: sensing each of N-1, and N-2 cardiac electrical events, where the N-1 cardiac electrical event precedes the Nth cardiac electrical event, and the N-2 cardiac electrical event precedes the N-1 cardiac electrical event, each of the Nth, N-1, and N-2 cardiac electrical events representing consecutive detections of cardiac events; observing an interval between the Nth and N-1 cardiac electrical events; determining amplitudes for each of the N-1 and N-2 cardiac electrical events; calculating a peak ratio as a ratio of the amplitude of the N-1 cardiac electrical event to the amplitude of the N-2 cardiac electrical event; determining whether the peak ratio falls within similarity range, and: if the peak ratio falls within the similarity range, characterizing the Nth cardiac electrical event as a T-wave if the interval is in an R-T interval range and otherwise characterizing the Nth cardiac electrical event as an R-wave; if the peak ratio is above the similarity range, characterizing the Nth cardiac electrical event as a T-wave if the interval is in the R-T interval range and otherwise characterizing the Nth cardiac electrical event as an R-wave; or if the peak ratio is below the similarity range, characterizing the Nth cardiac electrical event as an R-wave.

Additionally or alternatively, the method may further comprise calculating the R-T interval range by: sensing a reference cardiac electrical event; defining a refractory period and a T-wave period for identifying first and second peaks associated with the reference cardiac event; identifying a largest peak during the refractory period as the first peak; identifying a largest during the T-wave period as the second peak; determining an R-T interval for the reference cardiac event as the interval between the first and second peaks; and setting the R-T interval range around the R-T interval.

Additionally or alternatively, the method may further comprise calculating the R-T interval range by: sensing a reference cardiac electrical event by observing a crossing of a cardiac event detection threshold by the cardiac electrical signal, and identifying a first point in time at the crossing; defining a T-wave period for identifying a T-wave peak; identifying a largest peak during the T-wave period, and identifying a second point in time at the largest peak during the T-wave period; determining an R-T interval for the reference cardiac event as the interval between the first point in time and the second point in time; setting the R-T interval range around the R-T interval.

Additionally or alternatively, the method may comprise sensing at least N-1 and N-2 cardiac electrical events, wherein the N-1 cardiac electrical event occurs after the N-2 cardiac electrical event and before the Nth cardiac electrical event.

Additionally or alternatively, the step of characterizing the Nth cardiac electrical event as either an R-wave or a T-wave comprises: calculating a rectified peak ratio for the N-1 and N-2 cardiac electrical events as a ratio of a maximum rectified peak of the N-1 cardiac electrical event to a maximum rectified peak of the N-2 cardiac electrical event; calculating a peak-to-peak ratio for the N-1 and N-2 cardiac electrical events as a ratio of the sum of the magnitudes of the maximum positive and negative peaks associated with the N-1 sensed cardiac electrical event to the sum of the magnitudes of the maximum positive and negative peaks associated with the N-2 cardiac electrical event; observing an interval between the Nth and N-1 cardiac electrical events; and: if the rectified peak ratio is in a first range, characterizing the Nth cardiac electrical event as a T-wave if the interval is in an R-T interval range and the peak-to-peak ratio is above a second threshold, or else characterizing the Nth cardiac electrical event as an R-wave; if the rectified peak ratio is below the first range, characterizing the Nth cardiac electrical event as an R-wave; if the rectified peak ratio is above the first range, characterizing the Nth cardiac electrical event as a T-wave if the interval is less than an R-T interval estimate and the peak-to-peak ratio is above the second threshold, or else characterizing the Nth cardiac electrical event as an R-wave.

Additionally or alternatively, the step of characterizing the Nth cardiac electrical event as either an R-wave or a T-wave comprises: observing an interval between the Nth and N-1 cardiac electrical events; determining amplitudes for each of the N-1 and N-2 cardiac electrical events; calculating a peak ratio as a ratio of the amplitude of the N-1 cardiac electrical event to the amplitude of the N-2 cardiac electrical event; determining whether the peak ratio falls within similarity range, and: if the peak ratio falls within the similarity range, characterizing the Nth cardiac electrical event as a T-wave if the interval is in an R-T interval range and otherwise characterizing the Nth cardiac electrical event as an R-wave; if the peak ratio is above the similarity range, characterizing the Nth cardiac electrical event as a T-wave if the interval is in the R-T interval range and otherwise characterizing the Nth cardiac electrical event as an R-wave; or if the peak ratio is below the similarity range, characterizing the Nth cardiac electrical event as an R-wave.

Additionally or alternatively, the method may further comprise sensing a N-1 cardiac electrical event preceding the Nth cardiac electrical event, wherein the step of characterizing the Nth cardiac electrical event as either an R-wave or a T-wave comprises: determining an interval from the N-1 cardiac electrical event to the Nth cardiac electrical event; comparing the interval to an R-T interval range; and if the interval is in the R-T interval range, characterizing the Nth sensed cardiac electrical event as a T-wave; else characterizing the Nth cardiac electrical event as an R-wave.

Additionally or alternatively, the R-T interval range and the R-T interval estimate are calculated by analysis of one or more cardiac cycles.

Additionally or alternatively, the R-T interval range and the R-T interval estimate are preset.

Another illustrative, non-limiting example takes the form of an implantable defibrillator comprising: a plurality of electrodes adapted for implantation in a patient and configured to receive cardiac electrical signals and/or issue defibrillation shocks; a housing having an hermetic seal; operational circuitry disposed in the housing, and coupled to the plurality of electrodes, the operational circuitry including a battery, analysis circuitry for analyzing cardiac signals from the electrodes, therapy delivery capacitors for storing energy for a defibrillation shock, a charger configured to charge the therapy delivery capacitors using power from the battery, and therapy output circuitry for issuing a defibrillation shock to the electrodes using energy stored on the therapy delivery capacitors; wherein the operational circuitry is configured to perform a method as in any of the preceding examples.

Additionally or alternatively, the implantable defibrillator may further comprise a lead coupled to the canister, wherein at least one of the plurality of electrodes is disposed on, or is a portion of, the housing, and at least one of the plurality of electrodes is disposed on the lead, wherein the lead is adapted for subcutaneous placement and the implantable defibrillator is a subcutaneous implantable defibrillator.

Additionally or alternatively, the implantable defibrillator may further comprise a a lead coupled to the canister, wherein at least one of the plurality of electrodes is disposed on, or is a portion of, the housing, and at least one of the plurality of electrodes is disposed on the lead, wherein the lead is adapted for transvenous placement with a portion thereof in the heart of a patient, and the implantable defibrillator is a transvenous implantable defibrillator.

Another illustrative, non-limiting example takes the form of a wearable defibrillator comprising: a vest carrying a plurality of electrodes and adapted to be worn by a patient such that at least two of the electrodes are placed in contact with the patient when so worn; operational circuitry coupled to the plurality of electrodes, the operational circuitry including a battery, analysis circuitry for analyzing cardiac signals from the electrodes, therapy delivery capacitors for storing energy for a defibrillation shock, a charger configured to charge the therapy delivery capacitors using power from the battery, and therapy output circuitry for issuing a defibrillation shock to the electrodes using energy stored on the therapy delivery capacitors; wherein the operational circuitry is configured to perform a method as in any of the preceding examples.

Another illustrative, non-limiting example takes the form of an automated external defibrillator comprising: a plurality of electrodes and adapted to be placed on the torso of a patient, at least two of the electrodes being paddle electrodes adapted for external defibrillation; operational circuitry coupled to the plurality of electrodes, the operational circuitry including a battery, analysis circuitry for analyzing cardiac signals from the electrodes, therapy delivery capacitors for storing energy for a defibrillation shock, a charger configured to charge the therapy delivery capacitors using power from the battery, and therapy output circuitry for issuing a defibrillation shock to the paddle electrodes using energy stored on the therapy delivery capacitors; wherein the operational circuitry is configured to perform a method as in any of the preceding examples.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 8-10 illustrate defibrillator shock delivery using methods of FIGS. 5-7;

DETAILED DESCRIPTION

Some of the detailed examples that follow focus on subcutaneous implantable defibrillators (SICD). However, the present invention is not limited to a particular defibrillator placement. Embodiments of the present invention may be used in a variety of defibrillator types, including implantable defibrillators (whether transvenous, subcutaneous, epicardial, substernal, etc.), wearable defibrillators, and automatic external defibrillators (AEDs). In any of these contexts there is a possibility of an output shock causing or accelerating an arrhythmia.

Typically a defibrillator functions by sensing cardiac signals, most often electrical signals though other signals (sounds, motion, blood pressure, oxygenation, etc.) may sometimes also be gathered. The cardiac signals are analyzed to determine whether an arrhythmia requiring defibrillation therapy is present, most often by counting cardiac cycles ("beats") to calculate a beat rate, while also observing various features of the cardiac signal shape ("morphology"), which may include matching to a template (whether by correlation, wavelet transform, principal component analysis, etc.) and observations of signal width and variation over time.

Counting cardiac cycles can be performed in a variety of ways. Some systems and proposals include capturing a block of cardiac signals and identifying repeating cycles therein, such as by autocorrelation. Most implantable systems currently use cycle detection methods on an ongoing basis by comparing the cardiac signal to a time-varying threshold; when the time-varying threshold is crossed, a new cardiac cycle may be declared. Each cardiac cycle comprises a plurality of "waves" with the major components named according to convention as the P-wave, the QRS complex, and the T-wave. Cardiac cycle detection often focuses on detecting R-waves as indicating the ventricular rate. Since the most dangerous arrhythmias are typically ventricular in origin, the R-wave is usually the main focus of cycle detection.

Figure 1:
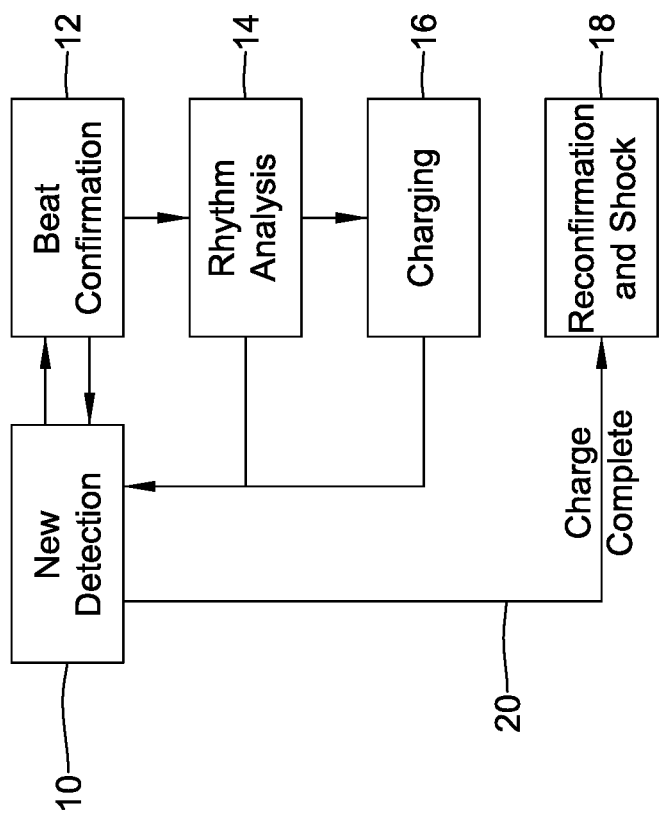
FIG. 1 illustrates a method of cardiac signal analysis in a defibrillator.

FIG. 1 illustrates a general method of cardiac signal analysis in a defibrillator. The method is iterative, and may initiate with the declaration of a new detection of a cardiac electrical event, as indicated at 10. The cardiac electrical event, once detected, may be called a "beat." Whether a new detection is cardiac in origin and/or properly counted may next be determined in beat confirmation 12. For example, noise and/or overdetection may be identified in block 12, causing rejection of the new detection and return to block 10.

If the beat is confirmed at 12, the method moves on to rhythm analysis. Some approaches to rhythm analysis rely on a beat rate calculation as a first tier of analysis. If the beat rate is above a ventricular fibrillation (VF) threshold, the most recently detected beat may be categorized as malignant. If the beat rate is in a ventricular tachyarrhythmia (VT) zone, the beat may be further analyzed using, for example, width, morphology or other factors, to differentiate sinus tachycardia (such as may accompany exercise) from ventricular tachycardia (whether monomorphic or polymorphic). If the beat rate is in the VT zone and the beat is found to result from ventricular tachycardia, the beat may again be categorized as malignant.

In some systems, rhythm analysis tracks a plurality of counters, such as by tracking monomorphic ventricular tachycardia (MVT) beats, VF beats, and normal beats. For example, one or more number of intervals to detect (NID) counters may be used; when the NID counter exceeds a defibrillation threshold, the method proceeds to block 16. In other systems, an X/Y filter may be used, where X tracks the number of malignant beats in a most recent set of Y confirmed beats. Again, if an X/Y threshold is met the method proceeds to block 16. If no condition requiring defibrillation therapy is present, the method returns to block 10 to await a next detection.

Block 16 makes reference to charging. Implantable and wearable defibrillators, as well as AED systems operate typically on battery power, with battery voltages that are much lower than the required voltage/power level needed for effective defibrillation. For example, the SICD system may output a defibrillation shock of 1350 volts with 80 joules of energy, using a battery source with an output voltage of about 9 volts; transvenous systems may have batteries with outputs of 3 or 6 volts while generating 40 joule shocks with 750 volts peak voltage. Wearable systems and AEDs may have bigger batteries, but also energy levels and voltages. Therefore each such defibrillator will use a charger to boost the battery output voltage to a much higher value, and stores the output of the charger on one or more therapy delivery capacitors until a therapeutic energy level is stored.

When charging is initiated at 16, the method returns to detection 10, and continues to cycle through blocks 10, 12, 14 and 16 until the charging procedure is completed. During charging, most modern systems continue to process beats in blocks 12 and 14 to ensure that arrhythmic conditions continue to be detected.

In existing systems, the path from beat detection to shock is different once the charging operation is completed. More particularly, after charging is complete, the next new beat detection from block 10 bypasses blocks 12 and 14. Instead, as indicated by line 20, the next new beat detection prompts reconfirmation and shock delivery 18.

Reconfirmation may include checking that the most recently sensed cardiac data continues to indicate a need for therapy, such as by determining whether the beat rate, as calculated using one or more intervals between detected beats just before charging is completed, is above a threshold. Some examples may include further reconfirmation criteria, such as disclosed in U.S. Pat. No. 9,149,637, the disclosure of which is incorporated herein by reference.

Some examples may have a two-part charging operation. First, charging is performed to a therapy threshold, typically a set voltage. Once the initial charging sequence is completed, reconfirmation is performed, such as using the methods in U.S. Pat. No. 9,149,637, or by capturing cardiac events and confirming beat rate is above a threshold, or by other criteria as desired. With reconfirmation completed, the capacitor charging restarts with a "top-off", since the reconfirmation may take up to several seconds during which leakage currents of the high voltage capacitors and related circuitry can reduce stored energy. The "top-off" occurs quickly (often less than 2 seconds, for example). When "top-off" is finished, synchronization is attempted by sensing for a new beat. If a new beat is detected, therapy is delivered; if no beat is detected during a preset time interval, an asynchronous defibrillation therapy is issued.

When the shock is delivered at 18 responsive to a new beat detection, this is considered a synchronized shock. If no new beat is detected after charging is completed for a predetermined period of time, existing systems will issue an asynchronous shock. For example, a 1 to 2 second delay (depending on the system) without a newly detected beat following charge completion can trigger the shock. In some contexts, this approach to shock delivery presents a hazard to the patient, as further illustrated below.

Figure 2:
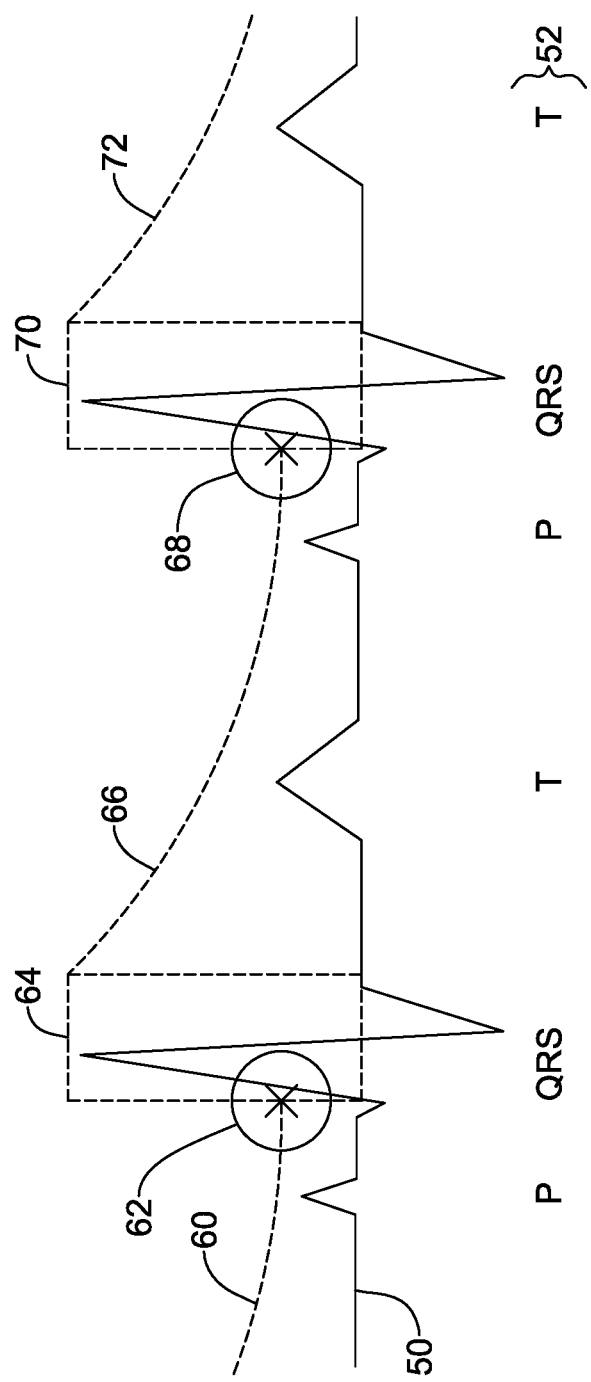
FIG. 2 illustrates graphically electrical cardiac event detection.

To understand the issue of pro-arrhythmia related to defibrillation shock, it is useful to first review how a defibrillator detects new beats. FIG. 2 illustrates graphically electrical cardiac event detection. The cardiac electrical signal is displayed at 50, with the conventional notations of P, QRS, and T waves shown at 52 aligned with components of the signal 50. A "detection profile" is applied as a series of dashed lines, including at the left side of the drawing a line 60 which continues over time until it crosses the cardiac signal line, at 62, an event that would be declared a detection of a new cardiac cycle or beat. Following detection 62, a refractory period is enforced as indicated at 64, during which no further beats can be declared. A detection period 66 follows refractory period 64, again decaying over time until another interaction with the cardiac electrical signal line at 68, prompting another refractory period 70, following by another detection period 72.

In use, the height of the detection profile during detection times (60, 66, 72) is typically proportional to the height of the detected events during the refractory periods 64, 70. For example, the detection period 66 may define a threshold for cardiac event detection starting at a first percentage of the R-wave height, which may be the peak during the refractory period 64, or one or more prior refractory periods, for example, calculated as a running average. A number of variations on this approach have been disclosed in the art, such as in U.S. Pat. Nos. 5,709,215 and 8,565,878 and US PG Pub. No. 20040049120, the disclosures of which are incorporated herein by reference.

Figure 3:
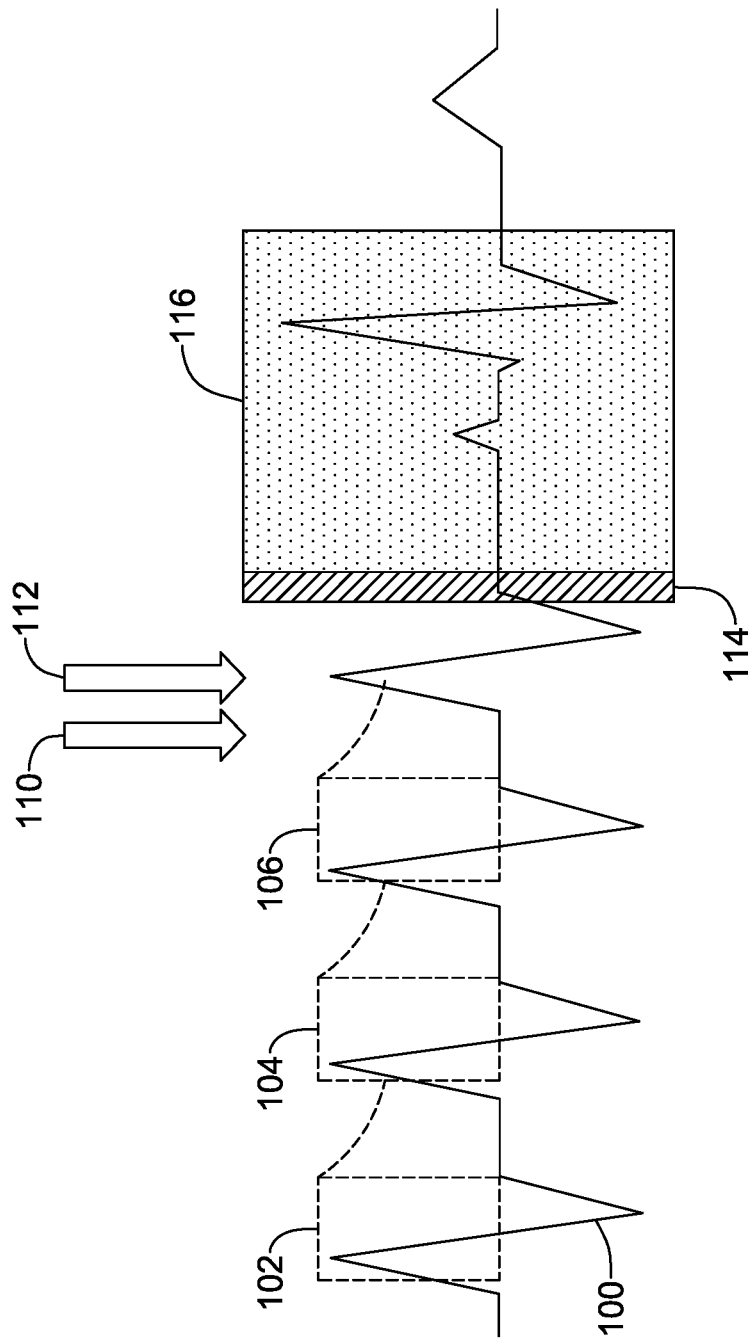
FIGS. 3-4 illustrate defibrillator shock delivery and effects on cardiac signals.
Figure 4:
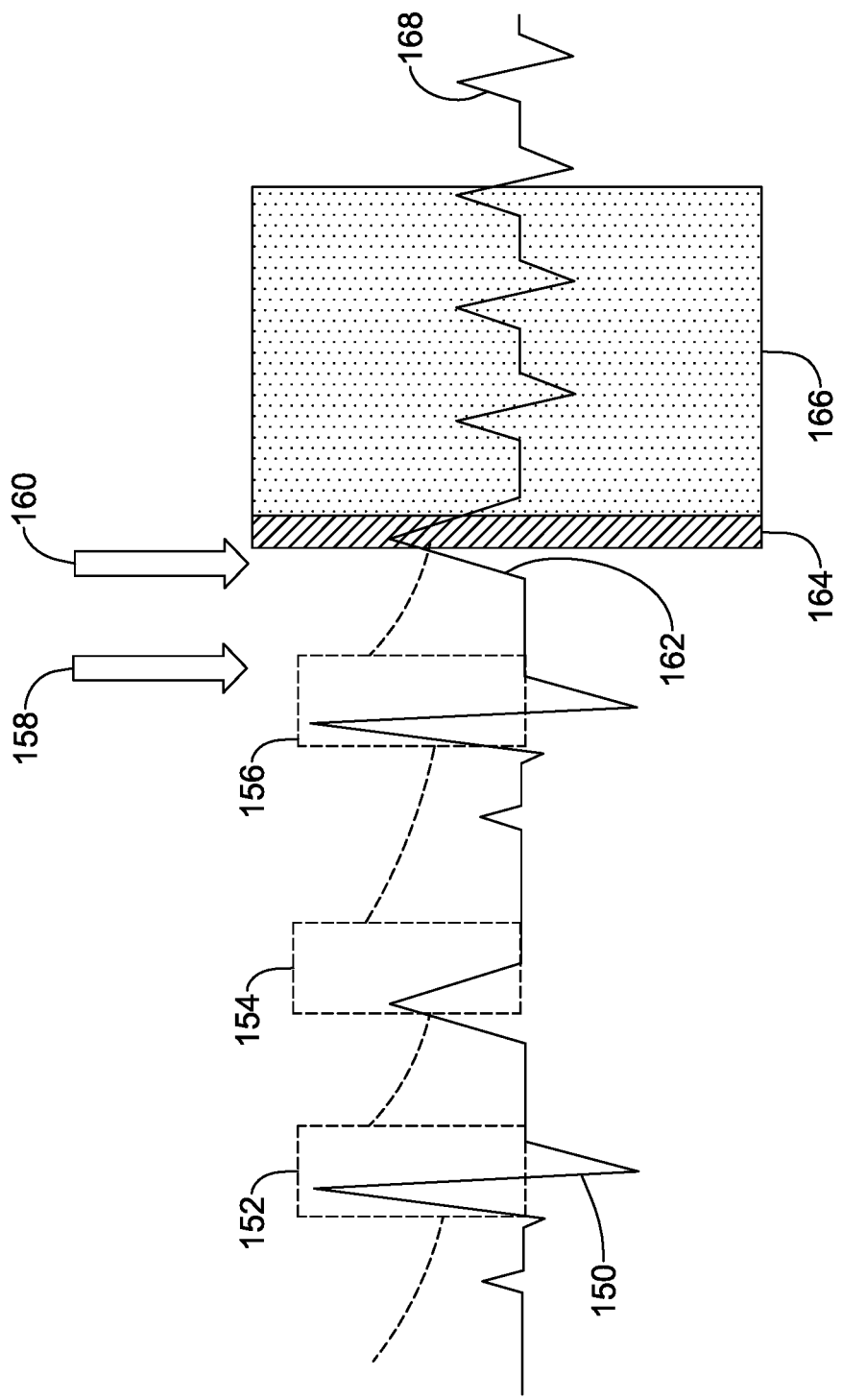

FIGS. 3-4 illustrate defibrillator shock delivery and effects on cardiac signals. FIG. 3 shows a positive outcome for the patient. The system processes the received cardiac signal 100 and detects new beats at 102, 104, 106, gleaning data that may be used to determine whether the arrhythmia to be treated continues to be detected. A charge end marker is indicated at 110, representing top-off in this example. The next beat to be detected occurs at 112, and the shock is delivered at 114. There may be a predetermined delay between detection 112 and shock delivery 114, if desired, typically less than 200 milliseconds or even shorter. In other examples shock 114 may follow more or less immediately (that is, as fast as any lag for the system to process the cardiac signal 100 and detect the event at 112 allows). Following shock delivery 114, a blanking period 116 may be enforced, during which the sensing circuitry of the defibrillator recovers from any transient electrical signals following the shock. In this example, the detected event at 112 is a fibrillation cycle, and the patient can be seen to convert to a more or less normal cardiac rhythm with a P-wave, QRS complex, and T-wave visible during and after the blanking period.

FIG. 4 shows a negative outcome for the patient. Here, the cardiac signal is shown at 150. The T-wave in the cardiac signal is prominent, more than half the size of the R-wave. This large T-wave causes overdetection of the cardiac signal, with detection 152 taking place on an R-wave, and detection 154 on a T-wave. If the underlying actual beat rate is, for example, in the range of about 90 bpm or higher, the detected signal can be double counted, causing the device to observe a beat rate of 180 bpm or higher. At such high (mis)calculated rates, the device is likely to identify a treatable condition and prepare to issue a shock.

In the illustration of FIG. 4, the shock end marker 158 occurs after the R-wave detection at 156 and prior to a subsequent T-wave detection at 162. If this occurs, the T-wave becomes the synchronizing event, and the shock issued at 164 can occur on the T-wave itself. The T-wave represents a vulnerable portion of the cardiac cycle, and a shock delivered on the T-wave can trigger the onset of VF, which is what happens in this example. Thus, during the blanking period 166 and thereafter, the patient experiences VF as shown at 168. This VF will then need to be treated by the defibrillator. Not only was the first shock unnecessary and as the result of T-wave oversensing, but a potentially deadly condition (VF) has been triggered, requiring further shocks. New and alternative approaches to the synchronization procedure shown in FIGS. 3-4 are desired.

Figure 5:
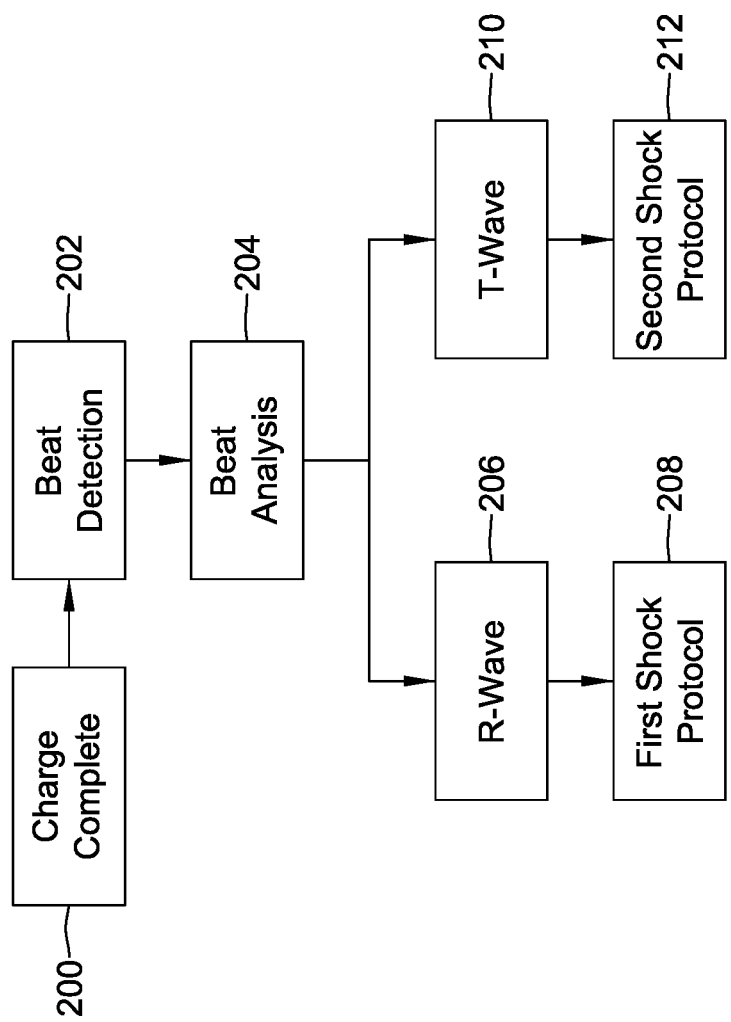
FIGS. 5-7 are block diagrams of new methods of defibrillation therapy delivery.
Figure 6:
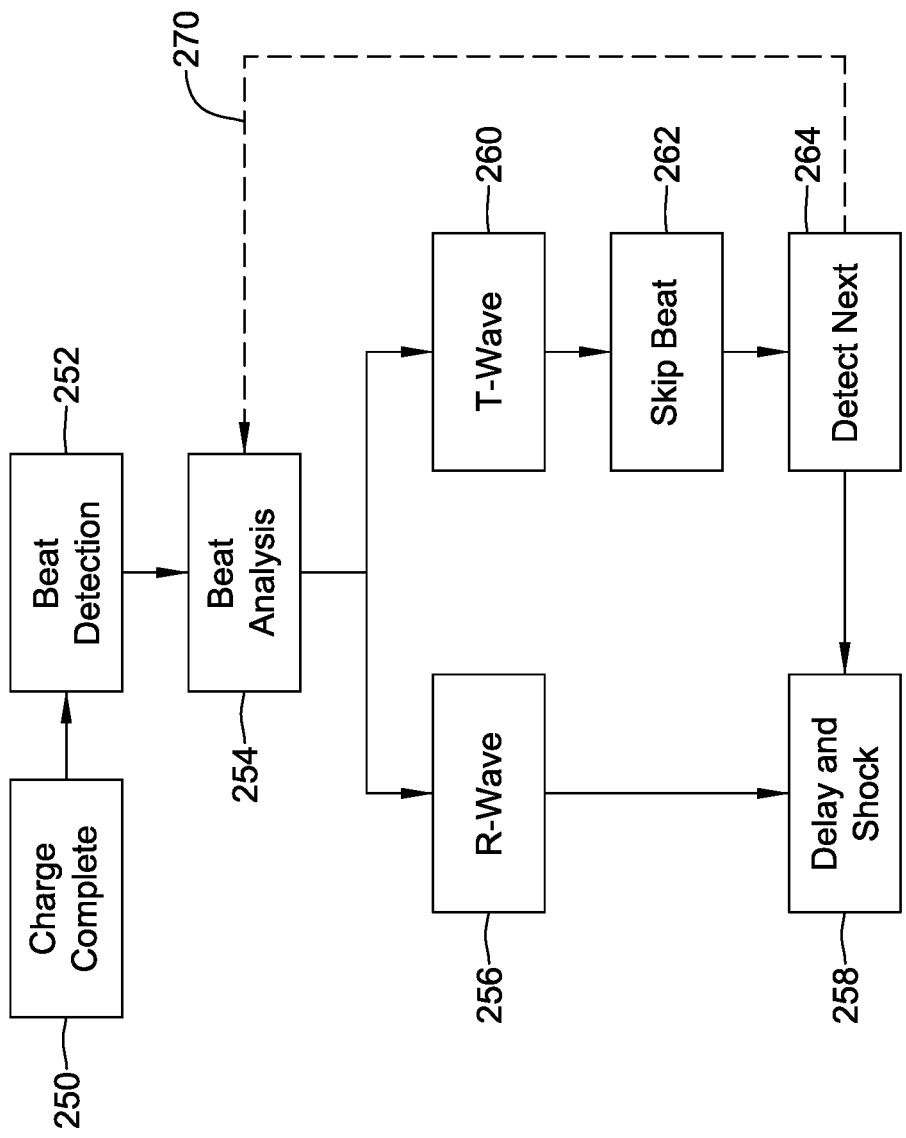
Figure 7:
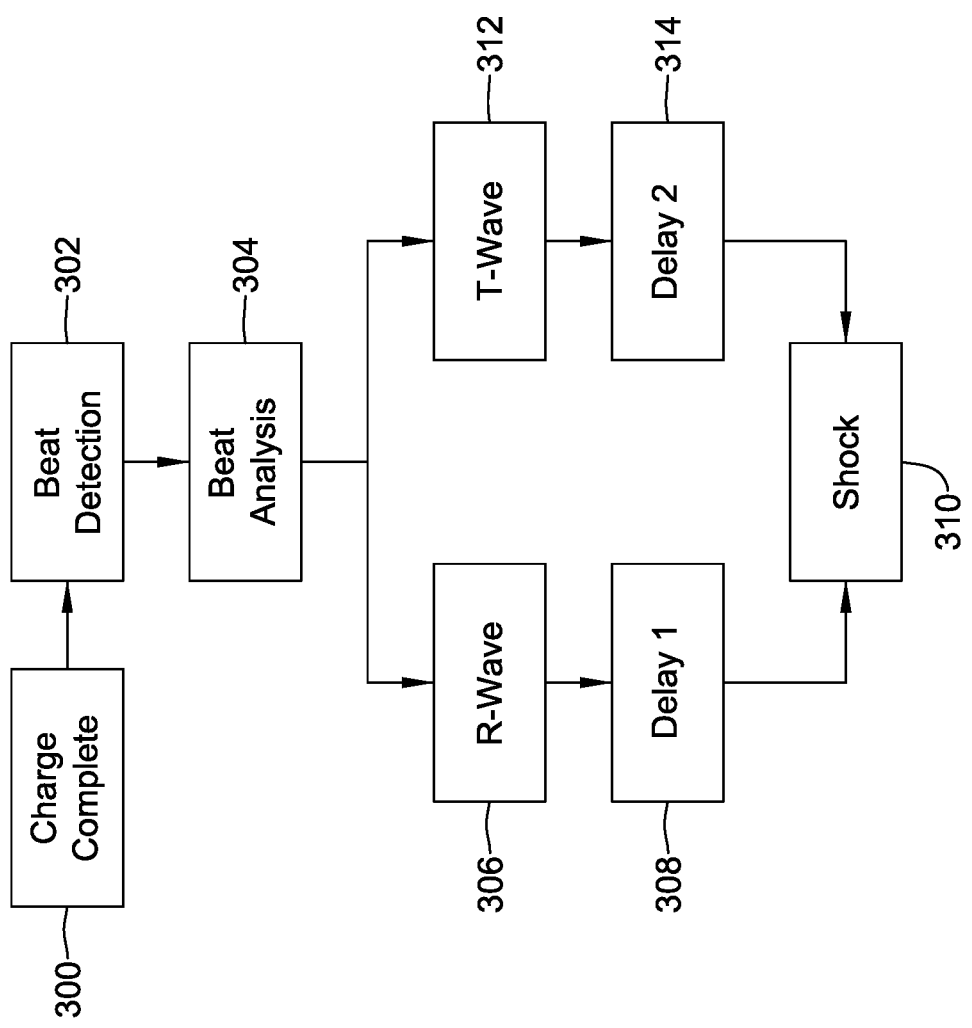

FIGS. 5-7 are block diagrams of new methods of defibrillation therapy delivery. In FIG. 5, a charge complete marker is noted at 200; for this and following examples the charge complete marker 200 may refer to completion of "top-off" as described above, though in other examples it may be an initial charge completion. The method proceeds to sense the cardiac signal in order to detect a next cardiac beat, at 202. When a beat is detected, the method proceeds to beat analysis 204. During beat analysis 204, the detected beat from block 202 is characterized as either an R-wave or a T-wave. If the beat is characterized as an R-wave, the method proceeds to block 206 and then executes a first shock protocol 208. If the beat is characterized as a T-wave, the method proceeds to block 210 and then executes a second shock protocol. The two shock protocols in the illustration are different from one another. In several examples, the second shock protocol at 212 delivers the shock later than the first shock protocol at 208, relative to the beat detected at 202. This may be due to waiting for a next detected beat, or by implementing a delay period, as illustrated in FIGS. 6 and 7, respectively.

It should be noted that the characterization performed in 204 is not necessarily a clinical determination. It may be the case that the detected beat at 202 is neither T-wave nor R-wave due to the absence of a sinus rhythm, as would be the case if fibrillation or certain ventricular tachyarrhythmias are taking place. The purpose is to characterize the beat in block 204 in order to determine which path to follow as between 206/208 and 210/212. Because the main impact of the additional analysis would be to avoid shocking on the T-wave, which itself would matter in the context where R and T waves are being overdetected, naming the characterization in block 204 as "R-wave" or "T-wave" is simply a convenient nomenclature. The characterization that results from the analysis at 204 may be performed using the steps illustrated and discussed in association with FIGS. 11-13, below, as well as other examples herein.

FIG. 6 shows another illustrative example. When charging is complete at 250, the method moves to beat detection 252. When a beat is detected, the method next performs beat analysis at 254, which results in the beat being characterized as either an R-wave or a T-wave. If the beat is characterized as an R-wave, the method goes to block 256 and then to block 258, where a delay and shock routine is performed. The delay in block 258 may be, for example and without limitation, a relatively short delay in the range of about 1 to about 350 milliseconds; in one illustration a delay from a synchronizing event is about 100 milliseconds. The delay may be omitted in some examples, with the shock simply being delivered at 258 immediately after the characterization of block 254 is completed.

If the beat is characterized as a T-wave in block 254, the method instead routes through block 260 to block 262, where the beat that has been characterized in block 254 as a T-wave is "skipped." By "skipped," what is meant is that no shock is delivered in synchronization to the beat that has been characterized as a T-wave. Instead, the method awaits a next detection, at block 264. When the next beat is detected in block 264, the method may directly go to block 258 to delay and issue the shock.

In an alternative example, as indicated at line 270, the next detected beat at 264 may again be subjected to the analysis of block 254. In some examples, a single "skip" beat is allowed and line 270 is omitted. In other examples, there may be two or more skipped beats, using line 270. To prevent extensive delay the method may only allow a maximum number of "skip" beats to take place, such as 2, 3 or 4 skipped beats, before automatically characterizing a beat as an R-wave and following path 256. In still other examples, there may be no maximum quantity of "skip" beats, but a maximum time to therapy after the charge completion block 250 can be enforced, such as limiting time between block 250 and block 258 to, for example, an interval in the range of about 1 to about 3 seconds. In practice, a maximum delay may be useful to ensure that shock energy remains above a threshold, since the high power capacitors used for shock delivery, as well as associated switches used to control therapy output, may each have leakage currents that will drain the stored energy to a point where therapy efficacy can be reduced. In still other examples, a repeated analysis at 254 that causes the path at 260/262 to be followed may be used to reopen the reconfirmation analysis, if desired, potentially averting the shock altogether.

The example in FIG. 6 may be characterized according to the language of FIG. 5, with the path at 256/258 serving as a first shock protocol, and the path of 260/262/264 (with possible repeats), then to 258, as a second shock protocol.

FIG. 7 shows another example. The method against starts at block 300 with charging complete, followed by beat detection 302. When a beat is detected, the beat is analyzed at 304 and characterized as either an R-wave 306 or a T-wave 308. If the beat is characterized as an R-wave 306, a first delay is enforced at 308 prior to shock delivery 310. The first delay may be a fixed delay, such as a delay in the range of 0 to 300 milliseconds, or about 100 milliseconds. In another example, the first delay may be a variable delay calculated using intervals between detected beats, or other factors. In one example, the first delay may be calculated using intervals between preceding detected events by determining an average of earlier detected events and subtracting, from the average, an interval between the beat detected at 302 and the beat that precedes it. The first delay may be sufficiently short in duration to be characterized as "immediately," that is, in the range of 300 milliseconds or less following either the detection of the beat or the characterization of the beat. The first delay may be as short as a single clock cycle in system using a digital clock as a reference for analytical steps.

If, instead, the detected beat is characterized as a T-wave in block 304, the method proceeds through block 312 and applied a second delay as indicated at 314 before issuing the shock at 310. The second delay may be a fixed delay that is longer than the first delay; for example, the second delay may be longer than the first delay by an amount in the range of 100 to 400 milliseconds. In one example, the second delay exceeds the first delay by 350 milliseconds. In another example, the first delay is 100 milliseconds and the second delay is 350 milliseconds. In still another example, the second delay is a variable delay calculated using intervals between detected beats. For example, the second delay may be calculated as the sum of two preceding intervals, less the interval between the beat detected at 302 and the beat that precedes it.

Several more particular calculations for the first and second delays are discussed in further detail below. FIG. 7 may be characterized using the language of FIG. 5, wherein the sequence of blocks 306, 308, 310 is a first shock protocol, and the sequence of blocks 312, 314, 310 is a second shock protocol.

Figure 10:
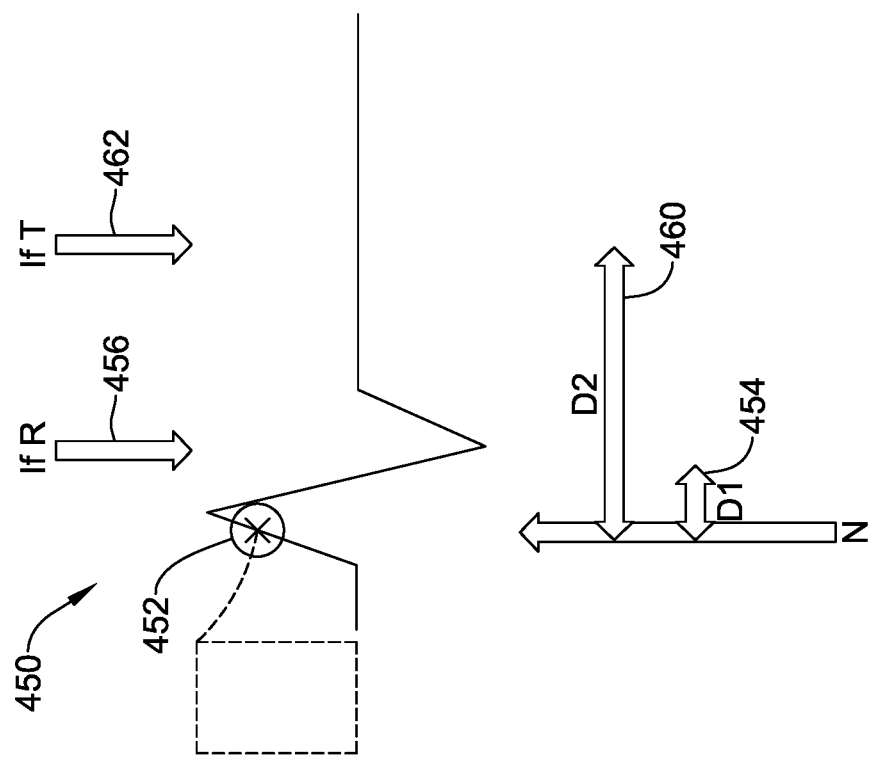

FIGS. 8-10 illustrate defibrillator shock delivery using methods of FIGS. 5-7. Each figure is shown in a manner assuming that capacitor charging (either initial or top-off, if top-off is part of the method) is completed. Starting with FIG. 8, example 350 shows a cardiac signal with a detected beat at 352. For naming purposes, the detected beat at 352 can be the "Nth" beat, and is the first detected beat following charge completion. Assuming no shock is delivered, a subsequent beat is detected at 360, and may be considered the N+1 beat. If the Nth beat 352 is characterized as an R-wave, a shock is delivered as shown at 354 (which would possibly mean that the N+1 beat 360 would not occur). If, on the other hand, the Nth beat 352 is characterized as a T-wave, the method would skip shock delivery on the Nth beat 352, and instead waits until detection of the N+1 beat at 360. Then the shock is issued as indicated at 362. To be clear, only one of the shocks 354, 362 would actually take place.

FIG. 9 shows another scenario. Here, again, the example 400 is shown as occurring after capacitor charging (and/or top-off) is completed. A detected beat takes place at 402. Beat 402 is analyzed to characterize it as either an R-wave or a T-wave. If beat 402 is characterized as an R-wave, the shock is promptly delivered at 404. If beat 402 is characterized as a T-wave, the method returns to sensing for another cardiac beat detection. In this example, no further beat is detected before a timeout 406 occurs. The timeout 406 may be calculated based on a time from the charge ending (not shown in the diagram), or, as illustrated in the graphic, from the time of detection of the beat at 402. The timeout 406 triggers an asynchronous shock delivery at 408. An illustrative timeout 406 may be at one second, though a range from about 500 milliseconds to 2.5 seconds is envisioned, or longer if desired. The timeout 406 may have a duration selected to prevent excessive drop in the therapy energy level due to leakage currents. To clarify, only one of the two shocks 404, 408 is actually delivered.

While FIGS. 8-9 generally correspond to the method shown in FIG. 6, FIG. 10 shows an example that corresponds to FIG. 7. The example 450 in FIG. 10 again starts after capacitor charging is completed. A detected beat occurs at 452, and that beat 452 is analyzed to characterize it as either an R-wave or a T-wave. If beat 452 is characterized as an R-wave, the shock is delivered as shown at 456, following expiration of a relatively shorter first delay period 454. If beat 452 is characterized as a T-wave, the method waits for expiration of a relatively longer second delay period 460 and delivers the shock at 462. In this example, it does not matter whether a second beat is detected following beat 452. To be clear, only one of the shocks 456, 462 occurs.

The first delay period 454 may be fixed, or it may be variable, and may be similar to that described above for Delay 1 308 in FIG. 7. A physician may be asked to select the first delay period 454 in some examples. If variable, the first delay period may be determined using any suitable methods. For example, the first delay period 454 may be calculated in advance by calculating an R-wave width during normal cardiac activity, or a width of detected beats during the ongoing arrhythmia, if desired. The first delay period 454 can then be calculated as a fraction, for example 25% to 125% of the calculated width, or about 80% to about 100% of the calculated width, for example. The first delay period 454 may instead be calculated using intervals between detected events, such as by averaging ongoing intervals and subtracting the interval immediately preceding the detected beat 452 from the average.

Likewise, the second delay period 460 may be fixed, or it may be variable. The second delay period 460 is preferably longer than the first delay period. For example, the second delay period 460 may be longer than the first delay by an amount in the range of 100 to 400 milliseconds. In one example, the second delay period 460 exceeds the first delay by 350 milliseconds, with the first delay period being fixed or variable. In another example, the first delay is 100 milliseconds and the second delay is 350 milliseconds with both being fixed. In another example, the second delay period is fixed and in a range of about 100 to about 400 milliseconds. In still another example, the second delay is a variable delay calculated using intervals between detected beats. For example, the second delay may be calculated as the sum of two preceding intervals, less the interval between the beat detected at 302 and the beat that precedes it. In another example, the second delay is determined by calculating a T-wave width by analyzing cardiac cycles detected during a normal cardiac rhythm, either as a fraction of the T-wave width, the entirety of the T-wave width, or the entire T-wave width plus a fraction of the T-wave width and/or a fixed added delay.

Figure 11:
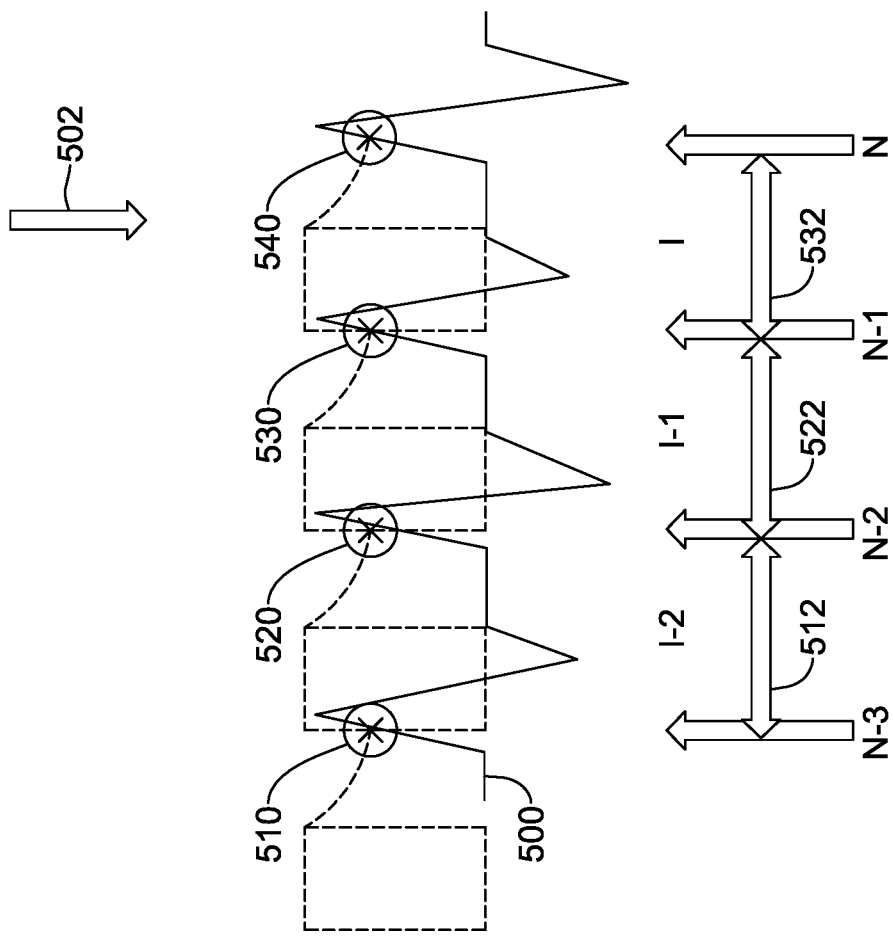
FIGS. 11-13 illustrate analytical steps for characterizing R and T waves.
Figure 13:
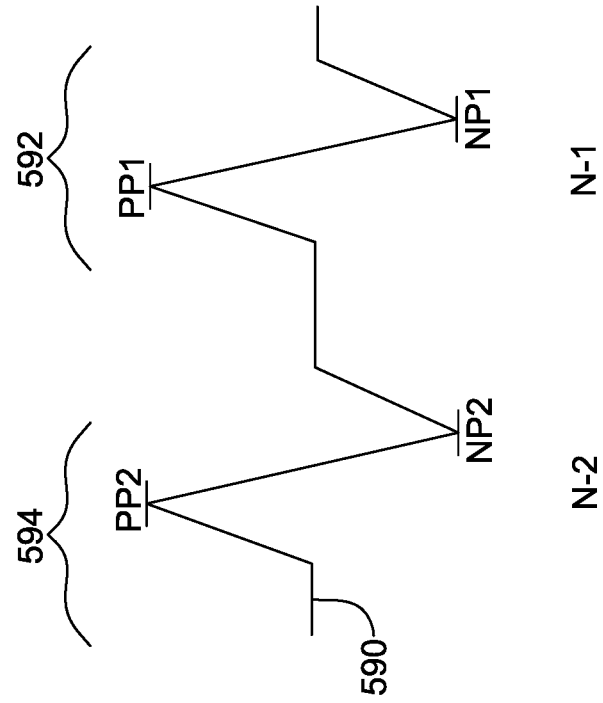
Figure 12:
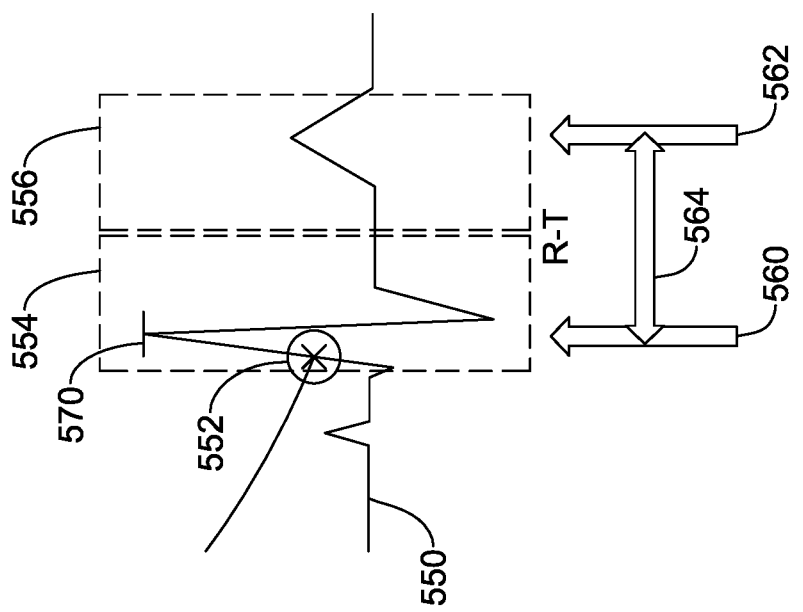

FIGS. 11-13 illustrate analytical steps for characterizing R and T waves. In FIG. 11 the labeling of detected events for purposes of analysis is illustrated. An illustrative cardiac signal is shown at 500, with the charge time ending at charge end marker 502. Because charge top-off may proceed rather quickly (<2 seconds in some examples), some of the beats 510, 520, 530 may occur before top-off charging is started. Several beats are detected at 510, 520, 530, 540, with beat 540 occurring after the charge end marker 502 and the others before it. These beats are labeled, using beat 540 as the reference point. Thus beat 540 is the Nth beat, beat 530 is the N-1 beat 532, beat 520 is the N-2 beat 522, and beat 510 is the N-3 beat. Intervals between the beats are labeled as intervals I 534, I-1 524, and I-2 514. When described in this manner herein, the N-2, N-1 and $N^{th}$ cardiac electrical events are consecutive detected cardiac electrical events, with N-2 being the earliest in time. This labeling will be used throughout the following discussion.

The intervals can be used in some examples to aid in characterizing the Nth beat 540 as an R-wave or as a T-wave. In one example, only interval 532 is analyzed by comparing it to an R-T interval range. If interval 532 is in the R-T interval range, then the Nth beat 540 can be characterized in this example as a T-wave; otherwise, the Nth beat 540 is characterized as an R-wave. Some further examples combine the interval analysis with analysis of the beats themselves, including the use of amplitude analysis, as detailed further below.

The intervals can also be used to determine shock delays as used in FIGS. 7 and 10. In an example, a first delay (the shorter delay used if the synchronizing beat is characterized as an R-wave) is calculated by determining an average of intervals I-1 522 and I-2 512, and subtracting interval I 532. The second delay can then be calculated by adding intervals I-1 522 and I-2 512, and subtracting interval I 532. Alternatively, the first delay can be a fixed delay, or the second delay can be a fixed delay, while still using the above calculations for the other of the two delays. In still another example, the first delay can be calculated using the above calculation, and the second delay determined by adding a fixed duration to the first delay. As noted previously, each of the first and second delays may instead be fixed delays.

FIG. 12 illustrates how an R-T interval may be calculated. A cardiac electrical signal is shown at 550, and a beat is detected at 552. A refractory period is defined at 554, and the R-wave is shown occurring within the refractory period. A T-wave detection period is then defined following the refractory period, as indicated at 556. For example, the refractory period may have a duration of 80 to 160 milliseconds, or more or less, and the T-wave period may have a duration of 120 to 200 milliseconds, or more or less. Preferably the sum of the refractory period 554 and T-wave detection period 556 is at least 300 milliseconds. In this context, the R-T interval is then calculated by identifying the peak (the R-wave peak) during the refractory period 554, as indicated by the arrow at 560, and the peak (the T-wave peak) during the T-wave detection period 556, as indicated by the arrow at 562, and calculating the interval 564 therebetween. In an alternative approach, the point in time of the detection at 552, where the detection threshold is crossed by the cardiac electrical signal, may be used as the start of the R-T interval, with the T-wave peak found during the T-wave detection period used as the end of the R-T interval instead.

The R-T interval can be calculated at any time for a given system. For example, for chronic devices (implants and wearables), at the time of fitting of the device or implantation of the device, the R-T interval may be calculated by a device using physician assistance to ensure correct peaks are flagged. In other examples, the R-T interval may be calculated, again for a chronic device, when rhythm analysis does not indicate the presence of any arrhythmia. In still other examples, the R-T interval may be "calculated" during an ongoing arrhythmia, for example, the arrhythmia (at least as identified by the device) that has triggered charging of the capacitors. While R-T interval calculation may be somewhat less reliable if attempted during an arrhythmia, the calculation can be performed nonetheless, if desired.

The R-T interval can then be used to set an R-T interval range useful for characterizing a detected beat as an R-wave or as a T-wave. For example, an R-T interval range may use the R-T interval as calculated in FIG. 12, plus/minus 20, 30, 40, 50, 60 or 70 milliseconds, or plus minus a percentage (10, 20, 30, 40, for example). Using the naming convention of FIG. 11, if the I interval 532 is in the R-T interval range, the Nth beat may be characterized as a T-wave, in an interval-only example. If desired, additional factors, such as amplitude or magnitude analyses, may be combined with the use of an R-T interval analysis.

FIG. 13 shows how amplitude peaks can be named for events N-1 and N-2. The cardiac signal 590 is shown, and two detected beats are shown at 592, 594, marked as N-1 592, and N-2 594. For each detected beat, positive and negative peaks are marked. Thus the N-1 beat 592 has a positive peak PP1 and a negative peak NP1, and the N-2 beat 594 has a positive peak PP2 and a negative peak PP2. These peaks can be used to analyze whether amplitudes or magnitudes suggest T-wave detection has occurred.

In an example, an analysis is performed to determine whether the beats 592, 594 show a big-little (that is, N-2 is "bigger" than N-1), little-big (that is, N-1 is "bigger" than N-2), or similar amplitude pattern. Each of big-little and little-big amplitude patterns suggest that an R-wave and a T-wave have been detected in sequence. In an example, the patterns may be determined by calculating one or more ratios. A rectified peak ratio can be calculated as:

Rectified Peak Ratio=max(|PP1|,|NP1|)/max(|PP2|,|NP2|)

A peak-to-peak ratio may also be calculated:

Peak-to-Peak Ratio=(|PP1|+|NP1|)/(|PP2|+|NP2|)

Where each of |PP1|, |NP1|, |PP2|, and |NP2| are the rectified peak amplitudes in each formula. Some examples may use only the rectified peak ratio and (referring again to FIG. 11) the I interval 532 as follows:
  a) If the Rectified Peak Ratio is within Similarity Bounds, the Nth beat is characterized as a T-wave only if I is within the R-T Interval Range and otherwise as an R-wave;
  b) If the Rectified Peak ratio is below the Similarity Bounds, the Nth beat is characterized as an R-wave; and
  c) If the Rectified Peak ratio is above the Similarity Bounds, the Nth beat is characterized as a T only if I is within or below the R-T Interval Range and otherwise as an R-wave Where the Similarity Bounds are defined as a range near 1, for example, 0.80 to 1.20, or higher or lower (anywhere from 0.65 to 0.99 as the lower bound, and 1.01 to 1.35 as the upper bound), as desired. The R-T interval range may be variable, such as by basing it on the calculation/analysis shown in FIG. 12, or may be fixed, such 200 to 300 milliseconds. As an alternative, each of the above at a), b) and c) may refer to the Peak-to-Peak Ratio instead. In still another alternative, both the Rectified Peak Ratio and the Peak-to-Peak Ratio are used, illustratively as follows:
  1) If the Rectified Peak Ratio is within Similarity Bounds, the Nth beat is characterized as a T-wave only if both the Peak to Peak ratio is above a Minimum and Interval I is within the R-T Interval Range; otherwise the Nth beat is characterized as an R-wave
  2) If the Rectified Peak ratio is below the Similarity Bounds, the Nth beat is characterized as an R-wave;
  3) If the Rectified Peak ratio is above the Similarity Bounds, the Nth beat is characterized as a T only if both the Peak-to-Peak Ratio is above a Minimum and Interval I is within or below the R-T Interval Range; otherwise the Nth beat is characterized as an R-wave Where Minimum is a lower bound set in the range of about 0.6 to about 0.9; in one example, Minimum is set to 0.8. In a further example, tests 1) and 2) may be as shown, and test 3) is modified to compare I to an R-T Interval Max value that is larger than the R-T interval range; for example, the R-T Interval Max may be 350 ms and the R-T interval range may be 200 to 300 milliseconds.

In another example, an R-T Interval Estimate (whether measured or pre-set) is used, and a two-tiered analysis takes place, as follows:
  i) If the Rectified Peak ratio is within Similarity Bounds, the Nth beat is characterized as an R-wave.

ii) If the Rectified Peak ratio is above Similarity Bounds, the Nth beat is characterized as a T-wave, unless Interval I is dissimilar to the R-T Interval Estimate.

iii) If the Rectified Peak ratio is below Similarity Bounds, the Nth beat is characterized as an R-wave unless Interval I is similar to the R-T Interval Estimate.

In this example, "similar to the R-T Interval Estimate" may mean a relatively close similarity, such as being within +/−50 milliseconds (though other boundaries in the range of about 10 to about 70 milliseconds may be used), while "dissimilar to the R-T interval estimate" may mean a relatively wider dissimilarity, such as being more than +/−100 milliseconds away from the R-T Interval Estimate (again, other boundaries in the range of about 40 to about 120 milliseconds may be used). The dissimilar/similar boundaries may in other examples be the same.

As can be appreciated, a number of different combinations of the intervals and amplitudes may be used. In another example, phase can be used to distinguish R-waves and T-waves. For example, the N-3, N-2 and N-1 detections may be characterized as either biphasic or monophasic by identifying the positive and negative peaks as shown in FIG. 13. A set of rules may be generated for characterizing each beat:

monophasic positive if PP>1.5*|NP|
monophasic negative if |NP|>1.5*PP
Otherwise biphasic Depending on the sensing vector used for sensing cardiac electrical signals, the QRS complex and the T-wave may fall into different categories amongst monophasic positive, monophasic negative and biphasic. If so, the polarity may be used to distinguish R and T waves as follows:

If Phase N-3=Phase N-1 and Phase N-2≠Phase N-1, and the Rectified Peak Ratio is above Similarity Bounds, the Nth beat is characterized as a T-wave;
Otherwise the Nth beat is characterized as an R-wave Whether such a feature is enabled may be dependent on whether the cardiac electrical signal (whether captured under physician supervision or in an ambulatory context), particularly the R-wave or QRS complex, is biphasic. For example, the defibrillator may sense one or more cardiac cycles before or during detection of an arrhythmia to determine whether the patient's cardiac signals associated with the R-wave (and/or the T-wave, optionally) are typically monophasic or biphasic. The T-wave is often monophasic in any event, and if the T-wave and R-wave are both of the same polarity for a given sensing vector, the analysis of phase to distinguish T-waves from R-waves may not be useful, so the system may enable or disable the use of phase to distinguish R-waves from T-waves as needed.

In another example, event shape may be used to differentiate R-waves from T-waves. Shape or morphology (terms that may be interchanged) can be analyzed using width, where width may be determined using methods described in U.S. Pat. No. 10,582,870, the disclosure of which is incorporated herein by reference. An R-wave or QRS complex is typically narrower than the T-wave, for example. If R-wave width is known for a given patient and defibrillator system (particularly with chronic devices such as wearable or implantable defibrillator systems), the N-1 detected event can be analyzed to see if it has a width matching that of an R-wave, in which case the Nth detection may be characterized as a T-wave if it falls within an R-T interval, for example. If the N-1 event does not match that of an R-wave, the Nth detection may be characterized as an R-wave for purposes of the methods of FIGS. 5-7.

Morphology can instead be analyzed an analysis such as correlation waveform analysis (CWA), in which a sample by sample comparison is made between a captured signal associated with a beat and a pre-stored, static or dynamic template. Morphology may rely on a transformation, such as a principal components analysis (PCA), or a wavelet transformation, in which components of the captured signal are first segregated and then compared to characterize similarity or dissimilarity. A frequency analysis, such as a Fast Fourier Transform (FFT) may be used to characterize detected beats. Using any such morphology analysis, the characterization of R-wave and T-wave can be performed by observing whether an alternating pattern can be identified and, if so, which of the N-3, N-2, and N-1 beats is likely to be an R-wave or a T-wave. Assuming consistent detection of cardiac events, it may further be inferred that if N-3 and N-1 are R-waves, and N-2 is a likely T-wave, then the Nth detection will also be a T-wave. The use of interval analysis (the R-T interval estimate or range) can be used in combination with such shape assessments.

For example, a rule set may be as follows:
If Shape N-3 is similar to Shape N-1 and Shape N-2 is not similar to Shape N-1, and the Rectified Peak Ratio is above Similarity Bounds, the Nth beat may be characterized as a T-wave;
Otherwise the Nth beat is characterized as an R-wave In this example, the shape similarity of N-3 to N-1, and dissimilarity to N-2, shows an alternating shape pattern. An alternating shape pattern, in turn, is suggestive of T-wave oversensing, and so the Rectified Peak Ratio is used here to determine whether the odd beats (N-3, N-1), or the event beats (N-2, N) are the likely R-waves. If instead N-3 and N-1 are not similar, no pattern can be gleaned and the analysis suggests that a randomly varying signal (such as a PVT or VF) is occurring, meaning that concerns of pro-arrhythmic shock are mitigated. If using morphology and no pattern is found, then the Nth detected event may automatically be characterized as an R-wave for purposes of the methods of FIGS. 5-7.

By comparing N-3 to N-1, as well as comparing N-2 to either of N-1 or N-3, the preceding example suggests a dynamic shape analysis in which the basis for comparison is constantly changing or updated with recent detection data. In a static analysis, a stored template or number may be used. For example, with width, one can compare N-3 to N-2 and/or N-1 in a dynamic analysis, or width of each of N-3, N-2, N-1 can be compared to a predetermined boundary to characterize beats as wide or narrow. With other shape analysis (CWA, PCA, Wavelet, or FFT), a static template can be stored, whether that is point-by-point data for CWA, component features for PCA, specific wavelets, or specific frequency components, where the analysis determines whether the beats match the stored static template. Then each beat can be categorized as matching or not matching, again to determine whether an alternating pattern exists.

It may be noted that in the examples so far, beat N is not itself analyzed for shape or amplitude, and only the interval preceding N is used in the analysis. The reason for omitting beat N is that the data coming in for beat N is incomplete when the analysis is triggered. For example, to synchronize a shock delivery to beat N may call for shock delivery before the data necessary to measure width or to perform any of CWA, PCA, Wavelet or FFT shape analysis is fully gathered.

In a further example, one or more features of beat N may be used as well, including in particular amplitude. Referring again to FIG. 12, given a detection 552, it may be possible to determine the amplitude shown at 570 by waiting for a turning point in the cardiac electrical signal before the shock delivery would be called for. If so, then amplitude 570 may be used in any of the above comparisons, for example, by observing whether a similarly placed in time peak for any of detections N-3, N-2, and N-1 has an amplitude that is similar to amplitude 570. Thus a rule set may be as follows:

If Amplitudes N-2, N-1 and N are low-high-low, and the amplitudes of N-1 and N-3 are similar, the Nth beat is characterized as a T-wave; or If Amplitude N-1 is greater than amplitude N, and Interval I is within the R-T Interval Range, the Nth beat is characterized as a T-wave;

Otherwise the Nth beat is characterized as an R-wave

Other factors and combinations of factors may be used instead to characterize the Nth beat as an R-wave or a T-wave. The various illustrations provides are not intended to limit the invention to only these particular analyses.

Figure 14:
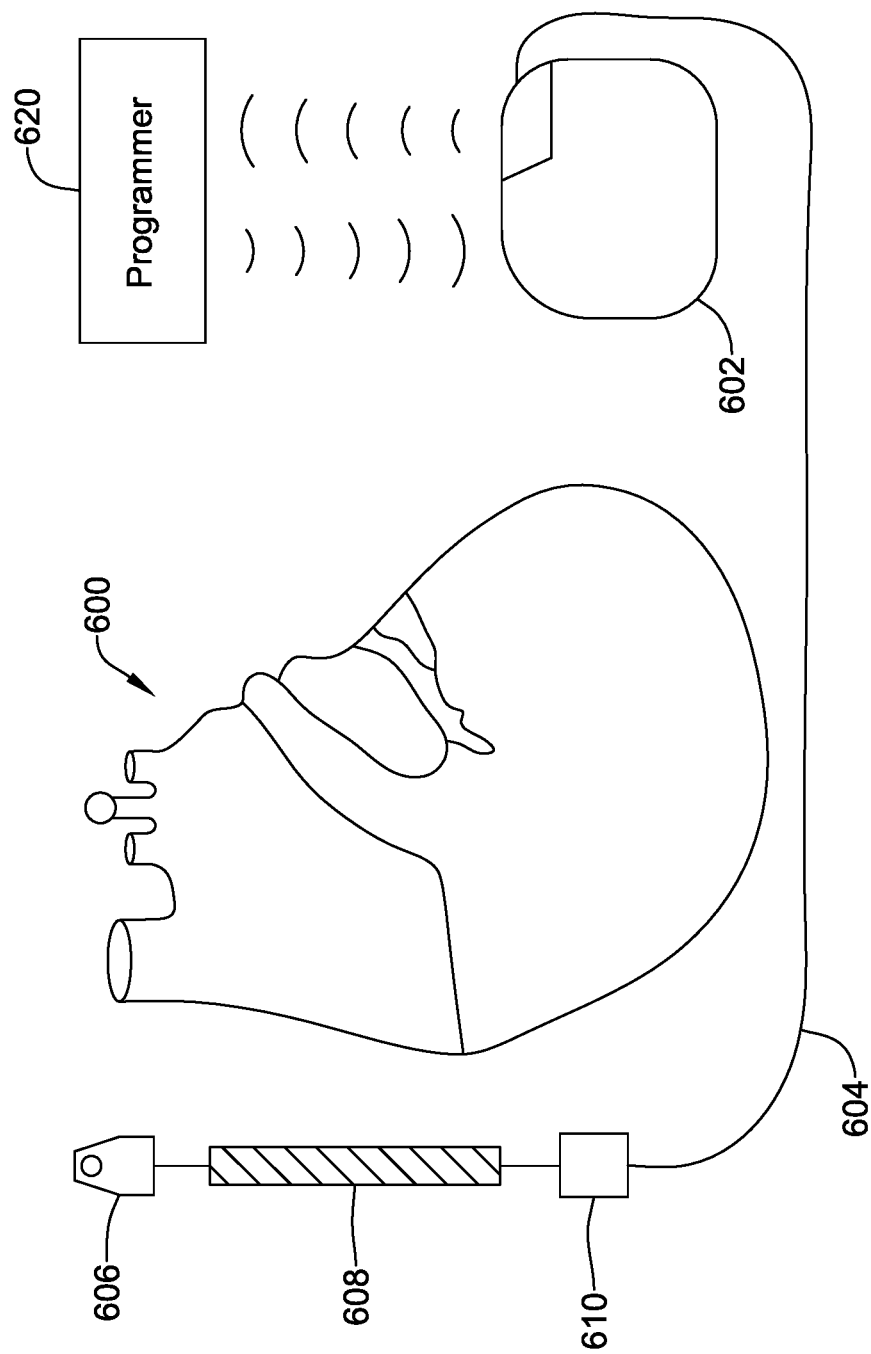
FIGS. 14-15 show illustrative implantable defibrillators.
Figure 15:
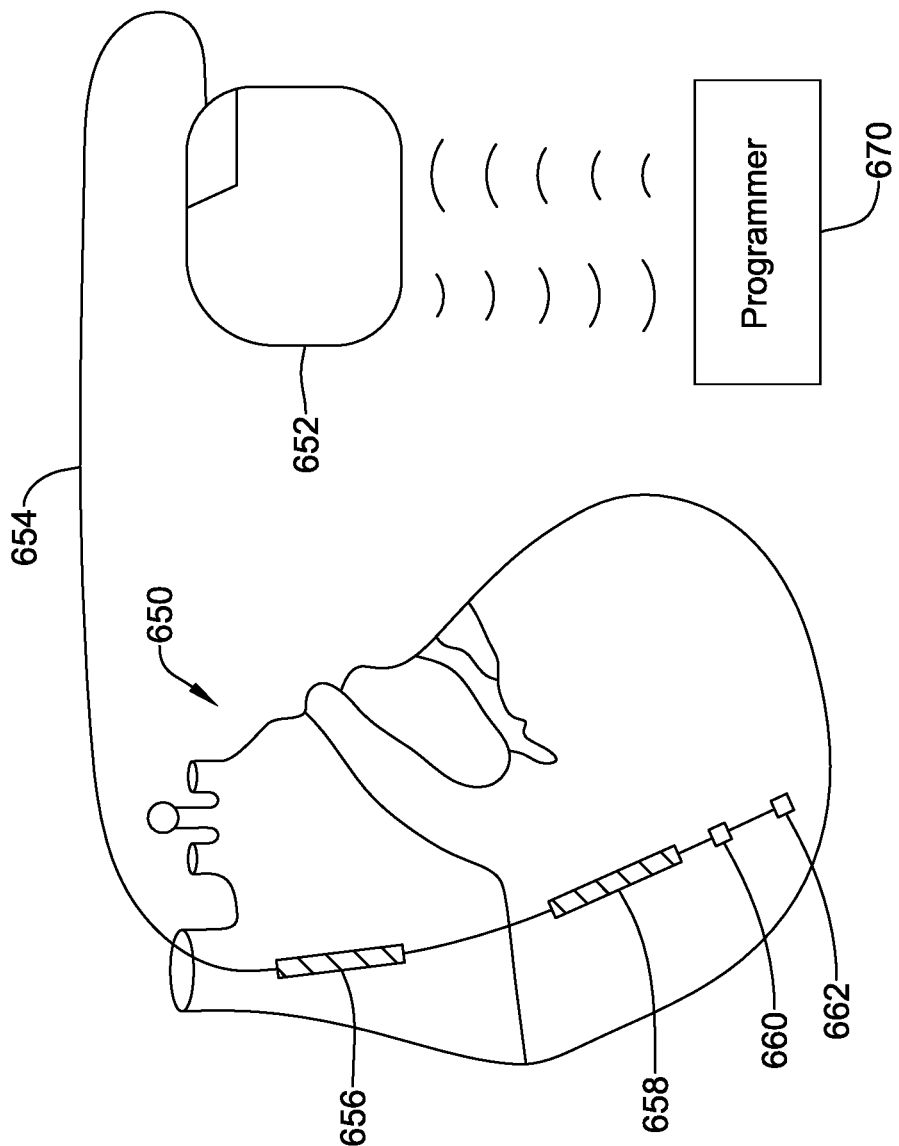

The present invention may find application in a wearable defibrillator system, an AED, or in an implantable system. Illustrative implantable systems are shown in FIGS. 14-15 as particular examples. Alternative implantable systems may include epicardial systems, or fully intravenous or intracardiac systems.

The illustrative system shown in FIG. 14 is shown relative to a heart 600. The system shown may be a subcutaneous implanted device such the Boston Scientific Emblem SICD System. The system in FIG. 14 may instead be implanted with the lead in a substernal position, or in the internal thoracic vein, as shown in various issued patents and/or published patent applications. A canister 602 may be implanted near the left axilla, with lateral, anterior, or posterior positions being possible. A lead 604 couples the canister 602 to electrodes 606, 608 and 610, which are illustrated as implanted along the sternum of the patient, typically to the left or right thereof. In other example the canister may be in an anterior position (axillary or pectoral, as desired), with the lead wrapping around to the posterior of the patient's chest. The system in FIG. 14 may include an external programmer 620 configured for communication with the implant 602.

The system in FIG. 10 is a transvenous system, illustratively shown relative to the heart 650 with the patient's ribs omitted for clarity. The canister 652 is in a high pectoral position, with the lead 654 accessing the vasculature, such as through the subclavian vein, and entering the heart. The lead 654 may include a superior vena cava coil electrode 656, a right ventricular coil electrode 658, and one or two ventricular sense/pace electrodes 660, 662. Again a programmer is shown at 670 and configured for communication with the implanted system. The system may further include a left ventricular lead (not shown).

Communication for either of the systems in FIG. 14 or 15 may be inductive, RF (such as using Medradio or Bluetooth) or via any other suitable medium of communication. Such communication can be useful to configure the implanted system for sensing, therapy or other feature, to load new software or firmware for the implanted system, and to retrieve information about system operation such as device status, therapy history, diagnostic data (both device and patient related), or other suitable data. The programmers may contain such circuitry as is needed to provide processing, memory, display, telemetry/RF communications and the like for these noted purposes.

Figure 16:
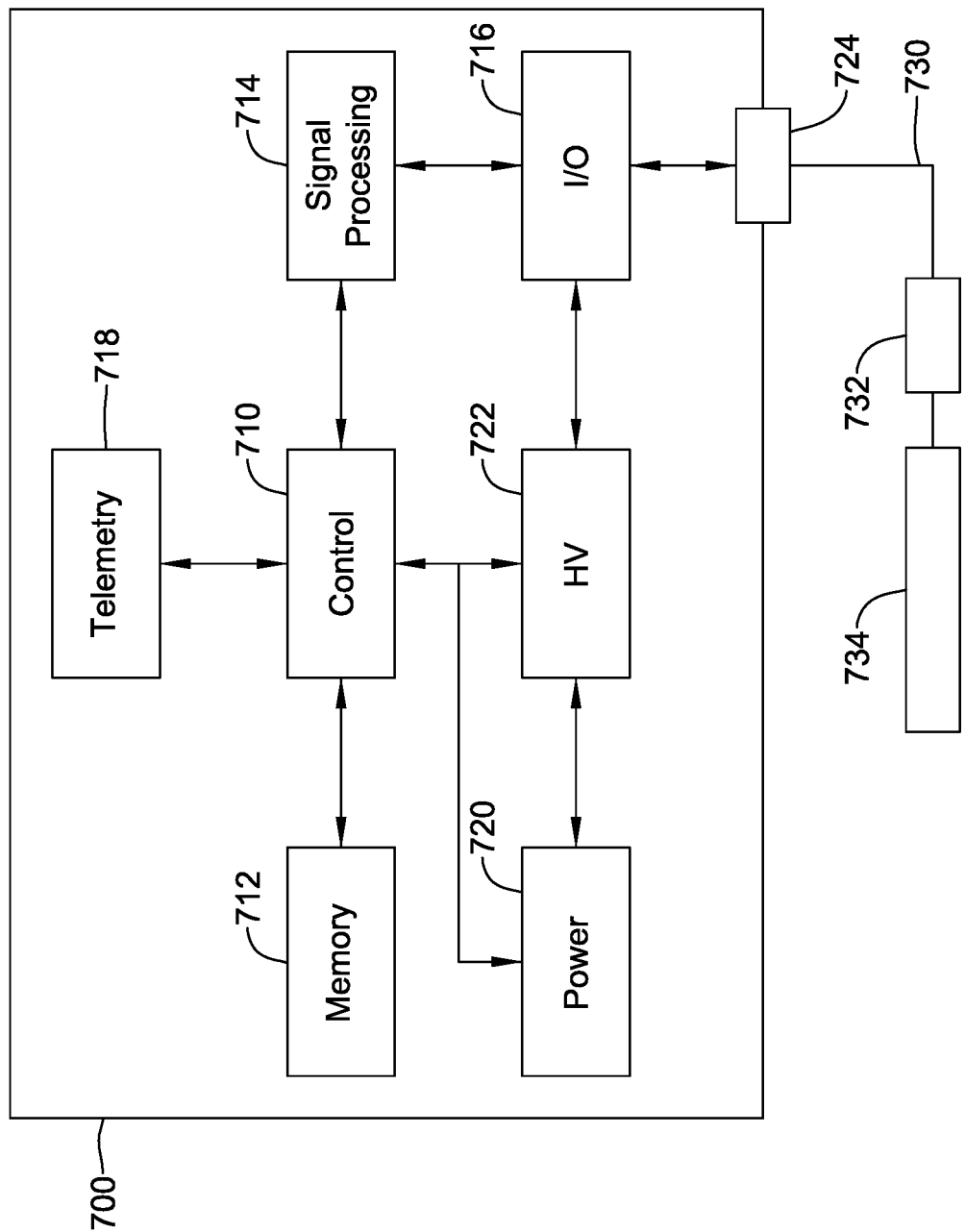
FIG. 16 illustrates operational circuitry of example defibrillators.

The canisters in FIGS. 14 and 15 will typically contain operational circuitry for the implantable system. FIG. 16 shows an illustrative example. A canister 700 houses operational circuitry including a control module 710 (which may be or include a microcontroller as well as various associated application specific integrated circuits (ASICs)). Memory 712 is provided to store operating data and instruction sets for operation of the control module 710. A signal processing portion is shown at 714 and may include suitable analog and/or digital circuits needed for signal processing of received cardiac electrical signals, including filtering, analog-to-digital conversion and any dedicated ASIC, such as a morphology analysis ASIC. The signal processing portion 714 is operably linked to an I/O component, which may include switching circuitry and DC and/or MRI blocking subcircuits, that in turn couple to a feedthrough and/or header 724.

The operational circuitry may also include a power source 720, such as a primary cell or rechargeable battery. A high voltage (HV) subcircuit is also provided as indicated at 722, and includes a charger and HV capacitors for use in defibrillation therapy. For example a charger may include voltage step up circuitry, such as a transformer, for generating high voltage outputs that are temporarily stored on HV capacitors for therapy purposes. The HV subcircuit 722 is also linked to the I/O 716. Control over the HV output may use an H-Bridge circuit, as are well known in the art.

One or more leads 730 may couple to the header 724. The lead or leads 730 may include one or more electrodes 732, 734 adapted for sensing and/or therapy delivery use. The canister 700 may be an hermetically sealed and conductive housing having one or more surfaces adapted for use as an electrode for therapy delivery or sensing purposes. A wearable defibrillator, or an AED, may have similar circuit elements and modules to those shown in FIG. 16, except to the extent that power levels for the output circuitry are higher, and the signal capture circuitry may be configured to capture surface signals for the cardiac ECG, which may resemble the signals captured by an SICD but typically at a lower signal voltage.

A wearable defibrillator may take the form of a vest, and may have electrodes built into a vest such that shock electrodes are placed anterior-posterior on the upper thorax of the patient, with or without a lateral (axillary position for example) electrode included; in some wearable defibrillator a dose of conductive gel can be expelled immediately prior to shock delivery if desired. The commercially available Zoll Lifevest is an example; additional examples including various vest designs appear in U.S. Pat. Nos. 5,944,669 and 6,065,154, the disclosures of which are incorporated herein by reference. Wearable defibrillators and AEDs may have an electronics module that is housed to protect the electronics, but do not necessarily have a conductive housing as is typical for implanted systems. Both wearable defibrillators and AEDs may have rechargeable batteries in some examples.

An AED, unlike the wearable defibrillator, will usually include electrodes on conductive leads that are placed on the patient without any sort of vest to carry such electrodes, with the electrodes typically adapted for placement on the anterior chest of the patient, with one electrode more lateral and inferior (usually to the left and below the heart) and the other electrode more superior and medial-to-right-sided. Various other specific design features of wearable and AED systems are well known to the skilled person. An example implementation of an AED is shown in U.S. Pat. No. 7,463,922, the disclosure of which is incorporated herein by reference. AEDs are commercially available including, for example, the Phillip's Heartstart AED and the Defibtech Lifeline, among others.

An illustrative, non-limiting example using reference to the above description and attached figures takes the form of a defibrillator apparatus (such as device 602, 652, and/or 700), comprising: a plurality of electrodes (606, 608, 610, and/or housing 602; 656, 658, 660, 662, and/or housing 652, or 732, 734, and/or housing 700) adapted to capture cardiac electrical signals and/or to deliver electrical therapy to a patient; output means (716, 722) for issuing defibrillation shocks using one or more of the electrodes, the output means comprising a charger and therapy delivery capacitors (722, wherein a charger and the capacitors may also take forms as described in U.S. Pat. No. 7,769,445, disclosed herein by reference); operational circuitry (710, 712, 714, 716) configured to detect and analyze cardiac cycles using cardiac electrical signals from the electrodes to sense cardiac events and determine whether and when to issue defibrillation shocks using the output means; wherein the operational circuitry is configured to perform the following: determining a need for a defibrillation shock (blocks 12 and 14 are used, in FIG. 1, to determine the need for a shock, causing block 16 to be called if shock is needed) and, if a defibrillation shock is needed, causing the output means to charge the therapy delivery capacitors to a predetermined shock threshold (block 16 in FIG. 1); after the therapy delivery capacitors are charged to the predetermined shock threshold (charge complete at 20 in FIG. 1, going to block 18 and leading to analysis as in FIGS. 5-7): sensing an $N^{th}$ cardiac electrical event (202, 252, 302); characterizing the $N^{th}$ cardiac electrical event as either an R-wave or a T-wave (204, 254, 304); and: if the $N^{th}$ cardiac electrical event is an R-wave (206, 256, 306), issuing the defibrillation shock according to a first shock protocol (208, 258, 308); or if the $N^{th}$ cardiac electrical event is a T-wave (210, 260, 312), issuing the defibrillation shock according to a second shock protocol (212, 262/264, 314).

Additionally or alternatively, the operational circuitry is configured such that issuing the defibrillation shock according to the first shock protocol comprises issuing the defibrillation shock after expiration of a first shock delay following the $N^{th}$ cardiac electrical event; and issuing the defibrillation shock according to the second shock protocol comprises issuing the defibrillation shock after expiration of a second shock delay following the $N^{th}$ cardiac electrical event. As discussed above, the first shock delay may nearly be immediate; a single clock cycle or up to 350 milliseconds delay may be used; in some examples the second delay is a fixed delay while in others the second delay may encompass waiting for other events to occur instead of or in addition to a fixed delay.

Additionally or alternatively, the operational circuitry is configured to set the second shock delay as follows: sensing each of N-1, N-2, and N-3 cardiac electrical events, where the N-1 cardiac electrical event precedes the Nth cardiac electrical event, the N-2 cardiac electrical event precedes the N-1 cardiac electrical event, and the N-3 cardiac electrical event precedes the N-2 cardiac electrical event, each of the $N^{th}$, N-1, N-2, and N-3 cardiac electrical events representing consecutive detections of cardiac events; determining interval I1, representing an interval from the N-1 cardiac electrical event to the $N^{th}$ cardiac electrical event; determining interval I2, representing an interval from the N-2 cardiac electrical event to the N-1 cardiac electrical event; determining interval I3, representing an interval from the N-3 cardiac electrical event to the N-2 cardiac electrical event; and setting the second shock delay equal to $\{I2+I3-I1\}$.

Additionally or alternatively the operational circuitry is configured to set the first shock delay equal to the greater of 0 or an average of I2 and I3, minus I1.

Additionally or alternatively the operational circuitry is further configured such that: issuing the defibrillation shock according to the second shock protocol comprises sensing for a Next cardiac electrical event during a predetermined timeout interval and either: if the Next cardiac electrical event is sensed during the predetermined timeout interval, issuing the defibrillation shock after detection of the Next cardiac electrical event, or issuing the defibrillation shock after expiration of a predetermined interval without sensing another cardiac electrical event.

Additionally or alternatively the operational circuitry is further configured such that: issuing the defibrillation shock according to the second shock protocol comprises sensing for a Next cardiac electrical event during a predetermined timeout interval and either: issuing the defibrillation shock after expiration of a predetermined interval without sensing another cardiac electrical event; or if the Next cardiac electrical event is sensed during the predetermined timeout interval, characterizing the Next cardiac electrical event as an R-wave or a T-wave, and: if the Next cardiac electrical event is an R-wave, issuing the defibrillation shock using the first shock protocol; or if the Next cardiac electrical event is a T-wave, either: sensing a Subsequent cardiac electrical event after the Next cardiac electrical event and issuing the defibrillation shock after detection of the Subsequent cardiac electrical event, or issuing the defibrillation shock after expiration of the predetermined timeout interval without sensing another cardiac electrical event after the Next cardiac electrical event.

Additionally or alternatively the operational circuitry is further configured to characterize the $N^{th}$ cardiac electrical event as either an R-wave or a T-wave by: sensing each of N-1, and N-2 cardiac electrical events, where the N-1 cardiac electrical event precedes the $N^{th}$ cardiac electrical event, and the N-2 cardiac electrical event precedes the N-1 cardiac electrical event, each of the $N^{th}$, N-1, and N-2 cardiac electrical events representing consecutive detections of cardiac events; observing an interval between the $N^{th}$ and N-1 cardiac electrical events; determining amplitudes for each of the N-1 and N-2 cardiac electrical events; calculating a peak ratio as a ratio of the amplitude of the N-1 cardiac electrical event to the amplitude of the N-2 cardiac electrical event; determining whether the peak ratio falls within similarity range, and: if the peak ratio falls within the similarity range, characterizing the $N^{th}$ cardiac electrical event as a T-wave if the interval is in an R-T interval range and otherwise characterizing the $N^{th}$ cardiac electrical event as an R-wave; if the peak ratio is above the similarity range, characterizing the $N^{th}$ cardiac electrical event as a T-wave if the interval is in the R-T interval range and otherwise characterizing the $N^{th}$ cardiac electrical event as an R-wave; or if the peak ratio is below the similarity range, characterizing the $N^{th}$ cardiac electrical event as an R-wave.

Additionally or alternatively, the operational circuitry is further configured to calculate the R-T interval range by: sensing a reference cardiac electrical event; defining a refractory period and a T-wave period for identifying first and second peaks associated with the reference cardiac event; identifying a largest peak during the refractory period as the first peak; identifying a largest during the T-wave period as the second peak; determining an R-T interval for the reference cardiac event as the interval between the first and second peaks; and setting the R-T interval range around the R-T interval.

Additionally or alternatively, the operational circuitry is further configured to calculate the R-T interval range by: sensing a reference cardiac electrical event by observing a crossing of a cardiac event detection threshold by the cardiac electrical signal, and identifying a first point in time at the crossing; defining a T-wave period for identifying a T-wave peak; identifying a largest peak during the T-wave period, and identifying a second point in time at the largest peak during the T-wave period; determining an R-T interval for the reference cardiac event as the interval between the first point in time and the second point in time; and setting the R-T interval range around the R-T interval.

Additionally or alternatively, the operational circuitry is further configured to sense at least N-1 and N-2 cardiac electrical events, wherein the N-1 cardiac electrical event occurs after the N-2 cardiac electrical event and before the $N^{th}$ cardiac electrical event.

Additionally or alternatively, the operational circuitry is configured to characterize the $N^{th}$ cardiac electrical event as either an R-wave or a T-wave by: calculating a rectified peak ratio for the N-1 and N-2 cardiac electrical events as a ratio of a maximum rectified peak of the N-1 cardiac electrical event to a maximum rectified peak of the N-2 cardiac electrical event; calculating a peak-to-peak ratio for the N-1 and N-2 cardiac electrical events as a ratio of the sum of the magnitudes of the maximum positive and negative peaks associated with the N-1 sensed cardiac electrical event to the sum of the magnitudes of the maximum positive and negative peaks associated with the N-2 cardiac electrical event; observing an interval between the $N^{th}$ and N-1 cardiac electrical events; and: if the rectified peak ratio is in a first range, characterizing the $N^{th}$ cardiac electrical event as a T-wave if the interval is in an R-T interval range and the peak-to-peak ratio is above a second threshold, or else characterizing the $N^{th}$ cardiac electrical event as an R-wave; if the rectified peak ratio is below the first range, characterizing the $N^{th}$ cardiac electrical event as an R-wave; if the rectified peak ratio is above the first range, characterizing the $N^{th}$ cardiac electrical event as a T-wave if the interval is less than an R-T interval estimate and the peak-to-peak ratio is above the second threshold, or else characterizing the $N^{th}$ cardiac electrical event as an R-wave.

Additionally or alternatively, the operational circuitry is configured to characterize the $N^{th}$ cardiac electrical event as either an R-wave or a T-wave by: observing an interval between the $N^{th}$ and N-1 cardiac electrical events; determining amplitudes for each of the N-1 and N-2 cardiac electrical events; calculating a peak ratio as a ratio of the amplitude of the N-1 cardiac electrical event to the amplitude of the N-2 cardiac electrical event; determining whether the peak ratio falls within similarity range, and: if the peak ratio falls within the similarity range, characterizing the $N^{th}$ cardiac electrical event as a T-wave if the interval is in an R-T interval range and otherwise characterizing the $N^{th}$ cardiac electrical event as an R-wave; if the peak ratio is above the similarity range, characterizing the $N^{th}$ cardiac electrical event as a T-wave if the interval is in the R-T interval range and otherwise characterizing the $N^{th}$ cardiac electrical event as an R-wave; or if the peak ratio is below the similarity range, characterizing the $N^{th}$ cardiac electrical event as an R-wave.

Additionally or alternatively, the operational circuitry is configured to sense a N-1 cardiac electrical event preceding the $N^{th}$ cardiac electrical event, and to characterize the $N^{th}$ cardiac electrical event as either an R-wave or a T-wave by: determining an interval from the N-1 cardiac electrical event to the $N^{th}$ cardiac electrical event; comparing the interval to an R-T interval range; and if the interval is in the R-T interval range, characterizing the $N^{th}$ sensed cardiac electrical event as a T-wave; else characterizing the $N^{th}$ cardiac electrical event as an R-wave.

Additionally or alternatively, the operational circuitry is configured such that the R-T interval range and the R-T interval estimate are calculated by analysis of one or more cardiac cycles. Additionally or alternatively, the operational circuitry is configured such that the R-T interval range and the R-T interval estimate are preset.

Additionally or alternatively, the operational circuitry is configured to characterize the $N^{th}$ cardiac electrical event as either an R-wave or a T-wave by detecting at least one preceding cardiac electrical event and determining whether one or more of an interval or an amplitude associated with the preceding cardiac electrical event indicates the $N^{th}$ cardiac electrical event is to be characterized as an R-wave or as a T-wave.

Additionally or alternatively, the operational circuitry is configured to characterize the $N^{th}$ cardiac electrical event as either an R-wave or a T-wave by detecting at least one preceding cardiac electrical event and analyzing morphology of the at least one preceding cardiac electrical event to characterize the $N^{th}$ cardiac electrical event as an R-wave or as a T-wave.

Additionally or alternatively, the defibrillator apparatus takes the form of a wearable defibrillator further comprising a vest carrying the electrodes.

Additionally or alternatively, the defibrillator apparatus takes the form of an automatic external defibrillator, wherein the electrodes are paddle electrodes.

Additionally or alternatively, the operational circuitry and output means are housed in a conductive canister, the canister serving as one of the electrodes, and one or more of the electrodes are also carried on a lead attached to the canister, the lead configured to pass through blood vessel and attach to the heart, such that the defibrillator apparatus takes the form of a transvenous implantable defibrillator.

Additionally or alternatively, the operational circuitry and output means are housed in a conductive canister, the canister serving as one of the electrodes, and one or more of the electrodes are also carried on a lead attached to the canister, the lead configured for subcutaneous placement, such that the defibrillator apparatus takes the form of a subcutaneous implantable defibrillator.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method of delivering a defibrillation shock in a defibrillator having electrodes for sensing cardiac signals, analysis circuitry for analyzing the sensed cardiac signals, therapy delivery capacitors for storing energy for the defibrillation shock, a charger configured to charge the therapy delivery capacitors, and therapy output circuitry for issuing the defibrillation shock using energy stored on the therapy delivery capacitors;

the method comprising:
determining a need for the defibrillation shock and charging the therapy delivery capacitors for defibrillation shock delivery to a predetermined shock threshold;
after completing charging of the therapy delivery capacitors to the predetermined shock threshold:
sensing an $N^{th}$ cardiac electrical event;
characterizing the $N^{th}$ cardiac electrical event as either an R-wave or a T-wave; and:

in response to a determination that the $N^{th}$ cardiac electrical event is characterized as an R-wave, issuing the defibrillation shock according to a first shock protocol; and
in response to a determination that the $N^{th}$ cardiac electrical event is characterized as a T-wave, issuing the defibrillation shock according to a second shock protocol;
further comprising sensing a N-1 cardiac electrical event preceding the $N^{th}$ cardiac electrical event, wherein the step of characterizing the $N^{th}$ cardiac electrical event as either an R-wave or a T-wave comprises:
determining an interval from the N-1 cardiac electrical event to the $N^{th}$ cardiac electrical event;
comparing the interval to an R-T interval range; and
in response to a determination that the interval is in the R-T interval range, characterizing the $N^{th}$ sensed cardiac electrical event as a T-wave;
else characterizing the $N^{th}$ cardiac electrical event as an R-wave.

2. The method of claim 1 wherein:
issuing the defibrillation shock according to the first shock protocol comprises issuing the defibrillation shock after expiration of a first shock delay following the $N^{th}$ cardiac electrical event; and
issuing the defibrillation shock according to the second shock protocol comprises issuing the defibrillation shock after expiration of a second shock delay following the $N^{th}$ cardiac electrical event.

3. The method of claim 2 further comprising calculating the second shock delay as follows:
sensing each of N-1, N-2, and N-3 cardiac electrical events, where the N-1 cardiac electrical event precedes the $N^{th}$ cardiac electrical event, the N-2 cardiac electrical event precedes the N-1 cardiac electrical event, and the N-3 cardiac electrical event precedes the N-2 cardiac electrical event, each of the $N^{th}$, N-1, N-2, and N-3 cardiac electrical events representing consecutive detections of cardiac events;
determining interval I1, representing an interval from the N-1 cardiac electrical event to the $N^{th}$ cardiac electrical event;
determining interval I2, representing an interval from the N-2 cardiac electrical event to the N-1 cardiac electrical event;
determining interval I3, representing an interval from the N-3 cardiac electrical event to the N-2 cardiac electrical event; and
setting the second shock delay equal to {I2+I3−I1}.

4. The method of claim 3 further comprising calculating the first shock delay equal to an average of I2 and I3, minus I1.

5. The method of claim 1 wherein issuing the defibrillation shock according to the second shock protocol comprises sensing a Next cardiac electrical event and:
issuing the defibrillation shock after detection of the Next cardiac electrical event, or
issuing the defibrillation shock after expiration of a predetermined timeout interval without sensing another cardiac electrical event.

6. The method of claim 1 wherein issuing the defibrillation shock according to the second shock protocol comprises sensing a Next cardiac electrical event and characterizing the Next cardiac electrical event as an R-wave or a T-wave, and:
in response to a determination that the Next cardiac electrical event is characterized as an R-wave, issuing the defibrillation shock using the first shock protocol after the Next cardiac electrical event; and in response to a determination that the Next cardiac electrical event is characterized as a T-wave, either:
sensing a Subsequent cardiac electrical event after the Next cardiac electrical event and issuing the defibrillation shock after detection of the Subsequent cardiac electrical event, or
issuing the defibrillation shock after expiration of a predetermined timeout interval without sensing another cardiac electrical event after the Next cardiac electrical event.

7. A method of delivering a defibrillation shock in a defibrillator having electrodes for sensing cardiac signals, analysis circuitry for analyzing the sensed cardiac signals, therapy delivery capacitors for storing energy for the defibrillation shock, a charger configured to charge the therapy delivery capacitors, and therapy output circuitry for issuing the defibrillation shock using energy stored on the therapy delivery capacitors; the method comprising:
determining a need for the defibrillation shock and charging the therapy delivery capacitors for defibrillation shock delivery to a predetermined shock threshold;
after completing charging of the therapy delivery capacitors to the predetermined shock threshold:
sensing an $N^{th}$ cardiac electrical event;
characterizing the $N^{th}$ cardiac electrical event as either an R-wave or a T-wave; and:
in response to a determination that the $N^{th}$ cardiac electrical event is characterized as an R-wave, issuing the defibrillation shock according to a first shock protocol; and
in response to a determination that the $N^{th}$ cardiac electrical event is characterized as a T-wave, issuing the defibrillation shock according to a second shock protocol;
wherein the step of characterizing the $N^{th}$ cardiac electrical event as either an R-wave or a T-wave comprises:
sensing each of N-1, and N-2 cardiac electrical events, where the N-1 cardiac electrical event precedes the $N^{th}$ cardiac electrical event, and the N-2 cardiac electrical event precedes the N-1 cardiac electrical event, each of the $N^{th}$, N-1, and N-2 cardiac electrical events representing consecutive detections of cardiac events;
observing an interval between the $N^{th}$ and N-1 cardiac electrical events;
determining amplitudes for each of the N-1 and N-2 cardiac electrical events;
calculating a peak ratio as a ratio of the amplitude of the N-1 cardiac electrical event to the amplitude of the N-2 cardiac electrical event;
determining whether the peak ratio falls within similarity range, and:
in response to a determination that the peak ratio falls within the similarity range, characterizing the $N^{th}$ cardiac electrical event as a T-wave when the interval is in an R-T interval range and otherwise characterizing the $N^{th}$ cardiac electrical event as an R-wave;
in response to a determination that the peak ratio is above the similarity range, characterizing the $N^{th}$ cardiac electrical event as a T-wave when the interval is in the R-T interval range and otherwise characterizing the $N^{th}$ cardiac electrical event as an R-wave; and
in response to a determination that the peak ratio is below the similarity range, characterizing the $N^{th}$ cardiac electrical event as an R-wave.

8. The method of claim 7 further comprising calculating the R-T interval range by:
sensing a reference cardiac electrical event;
defining a refractory period and a T-wave period for identifying first and second peaks associated with the reference cardiac event;
identifying a largest peak during the refractory period as the first peak;
identifying a largest peak during the T-wave period as the second peak;
determining an R-T interval for the reference cardiac event as the interval between the first and second peaks; and
setting the R-T interval range around the R-T interval.

9. The method of claim 7 further comprising calculating the R-T interval range by:
sensing a reference cardiac electrical event by observing a crossing of a cardiac event detection threshold by a cardiac electrical signal, and identifying a first point in time at the crossing;
defining a T-wave period for identifying a T-wave peak;
identifying a largest peak during the T-wave period, and identifying a second point in time at the largest peak during the T-wave period;
determining an R-T interval for the reference cardiac event as the interval between the first point in time and the second point in time; and
setting the R-T interval range around the R-T interval.

10. A method of delivering a defibrillation shock in a defibrillator having electrodes for sensing cardiac signals, analysis circuitry for analyzing the sensed cardiac signals, therapy delivery capacitors for storing energy for the defibrillation shock, a charger configured to charge the therapy delivery capacitors, and therapy output circuitry for issuing the defibrillation shock using energy stored on the therapy delivery capacitors; the method comprising:
determining a need for the defibrillation shock and charging the therapy delivery capacitors for defibrillation shock delivery to a predetermined shock threshold;
after completing charging of the therapy delivery capacitors to the predetermined shock threshold:
sensing an $N^{th}$ cardiac electrical event;
characterizing the $N^{th}$ cardiac electrical event as either an R-wave or a T-wave; and:
in response to a determination that the $N^{th}$ cardiac electrical event is characterized as an R-wave, issuing the defibrillation shock according to a first shock protocol; and
in response to a determination that the $N^{th}$ cardiac electrical event is characterized as a T-wave, issuing the defibrillation shock according to a second shock protocol;
further comprising sensing at least N-1 and N-2 cardiac electrical events, wherein the N-1 cardiac electrical event occurs after the N-2 cardiac electrical event and before the $N^{th}$ cardiac electrical event;
wherein the step of characterizing the $N^{th}$ cardiac electrical event as either an R-wave or a T-wave comprises:
observing an interval between the $N^{th}$ and N-1 cardiac electrical events;
determining amplitudes for each of the N-1 and N-2 cardiac electrical events;
calculating a peak ratio as a ratio of the amplitude of the N-1 cardiac electrical event to the amplitude of the N-2 cardiac electrical event;
determining whether the peak ratio falls within similarity range, and:

in response to a determination that the peak ratio falls within the similarity range, characterizing the $N^{th}$ cardiac electrical event as a T-wave when the interval is in an R-T interval range and otherwise characterizing the $N^{th}$ cardiac electrical event as an R-wave;

in response to a determination that the peak ratio is above the similarity range, characterizing the $N^{th}$ cardiac electrical event as a T-wave if the interval is in the R-T interval range and otherwise characterizing the $N^{th}$ cardiac electrical event as an R-wave; and in response to a determination that the peak ratio is below the similarity range, characterizing the $N^{th}$ cardiac electrical event as an R-wave.

* * * * *